US012172052B2

(12) United States Patent
Eder

(10) Patent No.: US 12,172,052 B2
(45) Date of Patent: Dec. 24, 2024

(54) SYSTEMS AND METHODS FOR PERSONALIZED EXERCISE PROTOCOLS AND TRACKING THEREOF

(71) Applicant: INCLUDEHEALTH, INC., Mason, OH (US)

(72) Inventor: James Ryan Eder, Columbus, OH (US)

(73) Assignee: INCLUDEHEALTH, Inc., Mason, OH (US)

( * ) Notice: Subject to any disclaimer, the term of this patent is extended or adjusted under 35 U.S.C. 154(b) by 69 days.

(21) Appl. No.: 18/134,281

(22) Filed: Apr. 13, 2023

(65) Prior Publication Data

US 2023/0249031 A1 Aug. 10, 2023

Related U.S. Application Data

(63) Continuation of application No. 17/375,518, filed on Jul. 14, 2021, now Pat. No. 11,654,332.

(60) Provisional application No. 63/188,053, filed on May 13, 2021, provisional application No. 63/162,121, filed on Mar. 17, 2021, provisional application No. 63/060,190, filed on Aug. 3, 2020, provisional application No. 63/051,982, filed on Jul. 15, 2020.

(51) Int. Cl.
*A63B 24/00* (2006.01)

(52) U.S. Cl.
CPC ...... *A63B 24/0062* (2013.01); *A63B 24/0006* (2013.01); *A63B 24/0075* (2013.01); *A63B 2024/0068* (2013.01); *A63B 2024/0071* (2013.01); *A63B 2220/05* (2013.01); *A63B 2220/806* (2013.01)

(58) Field of Classification Search
CPC ............ A63B 24/0006; A63B 24/0062; A63B 24/0068; A63B 24/0071; A63B 24/0075
See application file for complete search history.

(56) References Cited

U.S. PATENT DOCUMENTS

2019/0371114 A1 12/2019 Diefenbach et al.

OTHER PUBLICATIONS

Gardiner, Alexander; Extended European Search Report, issued in EP Pat. App. No. 21862314.8; Jun. 6, 2024; 13 pages.
Nekhai, Julia; "Startup of the day #11. First AI-powered Yoga assistant in your phone. Zenia app controls your home asana practice and gives real-time voice guidance"; Dec. 3, 2029; retrieved from https://startupjedi.vc/content/startup-day-11-first-ai-powered-yoga-assistant-your-phone-zenia-app-controls-your-home-asana.
Teh, Joe; "Kemtai AI Fitness is Here"; Jun. 22, 2020; retrieved from https://techielobang.com/blog/2020/06/22/kemtai-ai-fitness-is-here/.
YouTube Video: Zenia—Yoga Assistant; May 26, 2020; located at https://www.youtube.com/watch?v=ZH4BbR8Zi-A.
Facebook Video: Yoga with motion tracking on Zenia; Feb. 25, 2021; located at https://www.facebook.com/zeniayoga/videos/820455491899468/.

(Continued)

*Primary Examiner* — Reginald A Renwick
(74) *Attorney, Agent, or Firm* — Frost Brown Todd LLP

(57) ABSTRACT

Systems and methods for providing a customized exercise protocol to a computing device of a user. As the user performs the exercise protocol, one or more cameras of the computing device can track the user's movements. The user's movement are assessed to determine if proper form and technique is being used.

20 Claims, 38 Drawing Sheets

(56) References Cited

OTHER PUBLICATIONS

YouTube Video: The Best Virtual Training Platform | Kemtai; Feb. 14, 2020; located at https://www.youtube.com/watch?v=b2ohhuSRopo.
YouTube Video: Home Workout Using Motion Tracking | Kemtai; Jun. 29, 2020; https://www.youtube.com/watch?v=Wu21sEds_98.
YouTube Video: infiGro: The Revolutionary AI Personal Fitness Trainer; May 11, 2020; https://www.youtube.com/ watch?v=O1mtbPUxB9E.

SYSTEMS AND METHODS FOR PERSONALIZED EXERCISE PROTOCOLS AND TRACKING THEREOF

CROSS-REFERENCE TO RELATED APPLICATIONS

This application is a continuation of U.S. Ser. No. 17/375,518, filed on Jul. 14, 2021, which claims the benefit of U.S. Ser. No. 63/051,982 filed on Jul. 15, 2020; U.S. Ser. No. 63/060,190 filed on Aug. 3, 2020; U.S. Ser. No. 63/162,121 filed on Mar. 17, 2021; and U.S. Ser. No. 63/188,053 filed on May 13, 2021, the disclosure of each is incorporated herein by reference.

STATEMENT REGARDING FEDERALLY SPONSORED RESEARCH OR DEVELOPMENT

This invention was made with government support under contract FA8649-19-9-9904 awarded by the United States Air Force. The government has certain rights in the invention.

BACKGROUND

Various individuals can require physical therapy to regain mobility and maintain strength. Such individuals may be recovering from a surgical procedure, a stroke, a broken hip or limb or other debilitating disease or condition. The individual often has limited options with regard to where and when they can receive their physical therapy. For instance, the individual may be required to travel to a rehabilitation center or other type of healthcare or fitness center, but this approach can be inconvenient for the individual. Alternatively, a physical therapist or other service provider can travel to the individual's home to provide at-home physical therapy sessions, but this approach has numerous drawbacks as well.

Furthermore, aside from physical therapy, many individuals wish to perform physical exercises but may not want to travel to a training facility or are physically remote from their trainer. Such individuals may also not be able to structure their own exercise regimen or properly monitor their technique and form as they perform the exercises.

BRIEF DESCRIPTION OF THE DRAWINGS

It is believed that certain embodiments will be better understood from the following description taken in conjunction with the accompanying drawings, in which like references indicate similar elements and in which.

DETAILED DESCRIPTION

Figure 1:
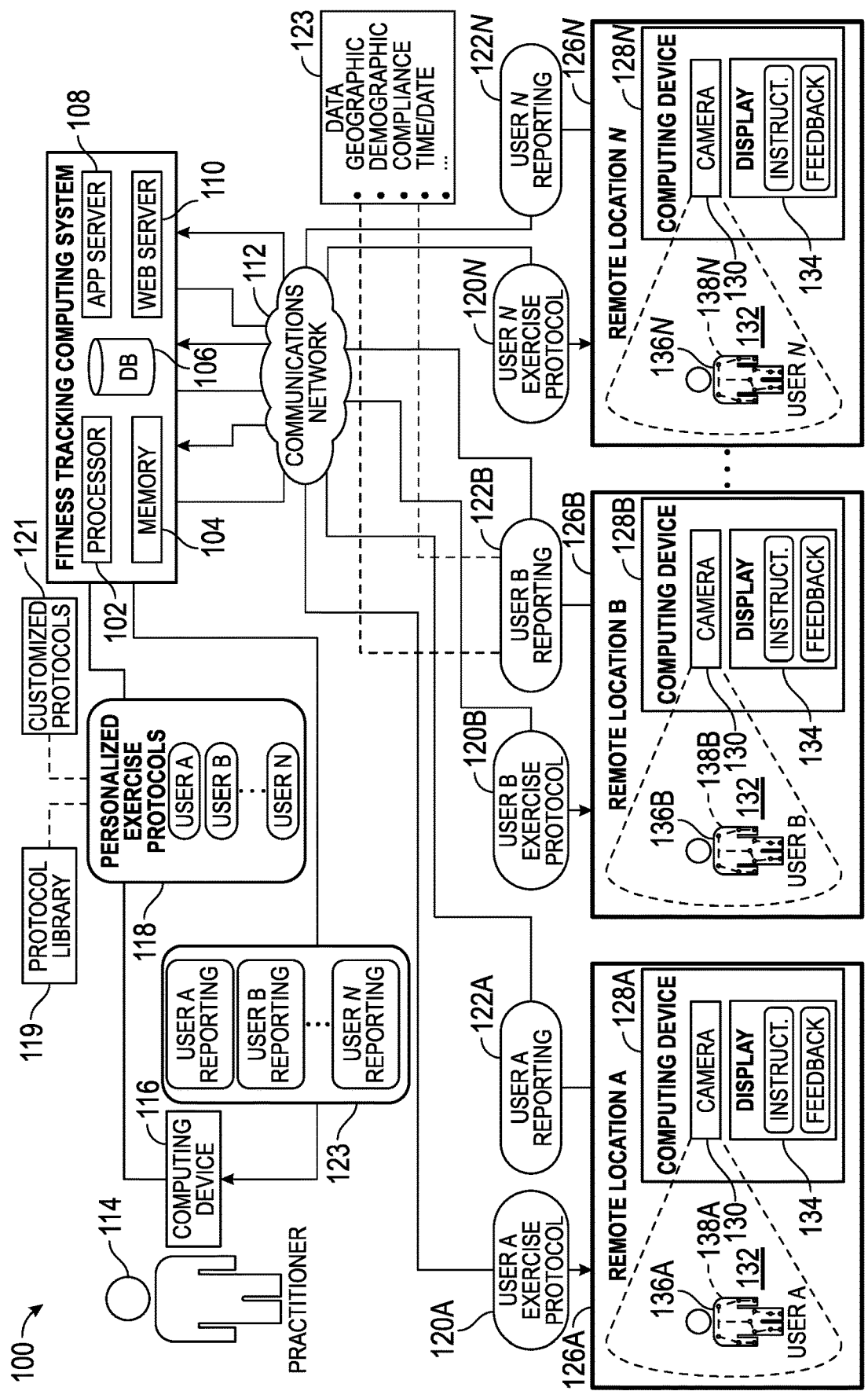
FIG. 1 schematically depicts a fitness tracking computing system facilitating remote exercise sessions in accordance with one non-limiting embodiment.

Various non-limiting embodiments of the present disclosure will now be described to provide an overall understanding of the principles of the structure, function, and use of systems, apparatuses, devices, and methods disclosed. One or more examples of these non-limiting embodiments are illustrated in the selected examples disclosed and described in detail with reference made to FIGS. 1-40 in the accompanying drawings. Those of ordinary skill in the art will understand that systems, apparatuses, devices, and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

The systems, apparatuses, devices, and methods disclosed herein are described in detail by way of examples and with reference to the figures. The examples discussed herein are examples only and are provided to assist in the explanation of the apparatuses, devices, systems and methods described herein. None of the features or components shown in the drawings or discussed below should be taken as mandatory for any specific implementation of any of these the apparatuses, devices, systems or methods unless specifically designated as mandatory. For ease of reading and clarity, certain components, modules, or methods may be described solely in connection with a specific figure. In this disclosure, any identification of specific techniques, arrangements, etc. are either related to a specific example presented or are merely a general description of such a technique, arrangement, etc. Identifications of specific details or examples are not intended to be, and should not be, construed as mandatory or limiting unless specifically designated as such. Any failure to specifically describe a combination or sub-combination of components should not be understood as an indication that any combination or sub-combination is not possible. It will be appreciated that modifications to disclosed and described examples, arrangements, configurations, components, elements, apparatuses, devices, systems, methods, etc. can be made and may be desired for a specific application. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

Throughout this disclosure, references to components or modules generally refer to items that logically can be grouped together to perform a function or group of related functions. Like reference numerals are generally intended to refer to the same or similar components. Components and modules can be implemented in software, hardware, or a combination of software and hardware. The term "software" is used expansively to include not only executable code, for example machine-executable or machine-interpretable instructions, but also data structures, data stores and computing instructions stored in any suitable electronic format, including firmware, and embedded software. The terms "information" and "data" are used expansively and includes a wide variety of electronic information, including executable code; content such as text, video data, and audio data, among others; and various codes or flags. The terms "information," "data," and "content" are sometimes used interchangeably when permitted by context. It should be noted that although for clarity and to aid in understanding some examples discussed herein might describe specific features or functions as part of a specific component or module, or as occurring at a specific layer of a computing device (for example, a hardware layer, operating system layer, or application layer), those features or functions may be implemented as part of a different component or module or operated at a different layer of a communication protocol stack. Those of ordinary skill in the art will recognize that the systems, apparatuses, devices, and methods described herein can be applied to, or easily modified for use with, other types of equipment, can use other arrangements of computing systems, and can use other protocols, or operate at other layers in communication protocol stacks, than are described.

The systems, apparatuses, devices, and methods disclosed herein generally relate to providing a customized exercise protocol to a computing device of a user. As the user performs the exercise protocol, one or more cameras of the computing device can track the user's movements. Machine vision technology, or any other suitable image processing technique, can be used to assess the user's movement to determine if proper form and technique is being used. In some embodiments, machine vision algorithms that identify and track joint locations of the user are utilized, although this disclosure is not so limited. Further, based on the movement tracking, it can be validated that the user performed the exercise protocol and such validation can be provided to a healthcare professional, trainer, physical therapist, rehabilitation specialist, or other practitioner, for example. As such, in accordance with the present disclosure, customized, user-specific exercise protocols can be delivered to individual users through any of a variety of different types of suitable networked computing devices. Example devices can include, without limitation, mobile phones, tablet computers, laptop computers, desktop computers, gaming devices, or any other device with a network connection and conventionally have one or more onboard cameras.

Beneficially, various embodiments of the systems and methods described herein can leverage the existing onboard camera of the user computing device, thereby avoiding the need for the user to install or otherwise utilize specialized camera systems or other specialized body tracking devices. As provided in more detail below, as users can interact with the system using a variety of different types of computing devices, such devices can have various screen sizes and be able to capture various levels of user data using onboard camera(s). The systems and methods described herein, however, can automatically detect operational parameters of the user computing devices through network communications with the user computing device and automatically and responsively make adjustments to the video processing technology on a per device basis.

Furthermore, it is to be appreciated that the systems and methods described herein can be used to provide customized fitness, physical therapy, work-outs, training sessions, or other wellness or exercise-related protocols to any type of user via any suitable device, with the user's compliance with the protocols being monitored via the image processing techniques described herein. In some embodiments, the user can additionally be instructed use various types of equipment, such as a kettlebell, a resistance band, a dumbbell, a jump rope, a jump box, and so forth. Thus, as is to be appreciated upon consideration of the present disclosure, a user's movements can be optically tracked such that various performance metrics can be collected, such as a range of motion, a number of repetitions, a number of sets, duration of repetitions, duration of sets, duration of workout, length of stroke, muscle group used, type of exercise, and so forth. Additionally, data can be collected from a wearable computing device worn by the user, such as a heartrate monitor, or other type of wearable fitness tracking device.

Referring now to FIG. 1, one example embodiment of the present disclosure can comprise a fitness tracking computing system 100. The fitness tracking computing system 100 can be provided using any suitable processor-based device or system, such as a personal computer, laptop, server, mainframe, or a collection (e.g., network) of multiple computers, for example. The fitness tracking computing system 100 can include one or more processors 102 and one or more computer memory units 104. For convenience, only one processor 102 and only one memory unit 104 are shown in FIG. 1. The processor 102 can execute software instructions stored on the memory unit 104. The processor 102 can be implemented as an integrated circuit (IC) having one or multiple cores. The memory unit 104 can include volatile and/or non-volatile memory units. Volatile memory units can include random access memory (RAM), for example. Non-volatile memory units can include read only memory (ROM), for example, as well as mechanical non-volatile memory systems, such as, for example, a hard disk drive, an optical disk drive, etc. The RAM and/or ROM memory units can be implemented as discrete memory ICs, for example.

The memory unit 104 can store executable software and data for the fitness tracking computing system 100. When the processor 102 of the fitness tracking computing system 100 executes the software, the processor 102 can be caused to perform the various operations of the fitness tracking computing system 100. Data used by the fitness tracking computing system 100 can be from various sources, such as a database(s) 106, which can be an electronic computer database, for example. The data stored in the database(s) 106 can be stored in a non-volatile computer memory, such as a hard disk drive, a read only memory (e.g., a ROM IC), or other types of non-volatile memory. In some embodiments, one or more databases 106 can be stored on a remote electronic computer system, for example. As is to be appreciated, a variety of other databases or other types of memory storage structures can be utilized or otherwise associated with the fitness tracking computing system 100.

The fitness tracking computing system 100 can also be in communication with a plurality of users 136A-N via their user computing devices 128A-N through a communications network 112. The users 136A-N can be, for example, individuals seeking physical therapy treatments, or any other type of user seeking exercise instruction. Each of the users 136A-N can be in a respective remote location 126A-N. The remote locations 126A-N can be, for example, their home, a fitness center, a rehabilitation center, a physical therapy center, and so forth. The fitness tracking computing system 100 can communicate with the various user computing devices 128A-N via a number of computer and/or data networks, including the Internet, LANs, WANs, GPRS networks, etc., that can comprise wired and/or wireless communication links.

The computing devices 128A-N can be any type of computer device suitable for communication with the fitness tracking computing system 100 over the communications network 112, such as a wearable computing device, a mobile telephone, a tablet computer, a device that is a combination handheld computer and mobile telephone (sometimes referred to as a "smart phone"), a personal computer (such as a laptop computer, netbook computer, desktop computer, and so forth), or any other suitable mobile communications device, such as personal digital assistants (PDA), tablet devices, gaming devices, or media players, for example.

The computing devices 128A-N can, in some embodiments, provide a variety of applications for allowing the users 136A-N to accomplish one or more specific tasks using the fitness tracking computing system 100. Applications can include, without limitation, a web browser application (e.g., INTERNET EXPLORER, MOZILLA, FIREFOX, SAFARI, OPERA, NETSCAPE NAVIGATOR), telephone application (e.g., cellular, VoIP, PTT), networking application, messaging application (e.g., e-mail, IM, SMS, MMS), social media applications, and so forth. The computing devices 128A-N can comprise various software programs such as system programs and applications to provide computing capabilities in accordance with the described embodiments. System programs can include, without limitation, an operating system (OS), device drivers, programming tools, utility programs, software libraries, application programming interfaces (APIs), and so forth. Exemplary operating systems can include, for example, a PALM OS, MICROSOFT OS, APPLE OS, ANDROID OS, UNIX OS, LINUX OS, SYMBIAN OS, EMBEDIX OS, Binary Runtime Environment for Wireless (BREW) OS, JavaOS, a Wireless Application Protocol (WAP) OS, and others.

The computing devices 128A-N can include various components for interacting with the fitness tracking computing system 100. The computing devices 128A-N can include components for use with one or more applications such as a stylus, a touch-sensitive screen, keys (e.g., input keys, preset and programmable hot keys), buttons (e.g., action buttons, a multidirectional navigation button, preset and programmable shortcut buttons), switches, a microphone, speakers, an audio headset, and so forth. The computing devices 128A-N can also each have a camera 130. The camera 130 can either be a single camera, or a collection of cameras, which have a field of view 132. In some embodiments, one or more of the computing devices 128A-N can also include a range finding device or other optical-related componentry that can be leveraged for movement tracking in accordance with the present disclosure. Additionally, the computing devices 128A-N can have a graphical display 134 to present information from the fitness tracking computing system 100. Such information can include, without limitation, movement instructions and real-time movement feedback. In accordance with various embodiments, the camera 130 and/or other onboard optical-related componentry can be standard equipment installed into the computing devices at time of manufacture. As such, a user does not necessarily have to install an additional camera or other hardware devices, or use other specialize hardware in order utilize the functionality of the fitness tracking computing system 100. Instead, the fitness tracking computing system 100 functions to responsively adapt to the type of computing device 128A-N that each user 136A-Nis using to connect to the system.

The users 136A-N can interact with the fitness tracking computing system 100 via a variety of other electronic communications techniques, such as, without limitation, HTTP requests, in-app messaging, and short message service (SMS) messages, video messaging, video chatting, and the like. The electronic communications can be generated by a specialized application executed on the computing devices 128A-N or can be generated using one or more applications that are generally standard to the user computing device 128A-N, such as a web browser. The applications can include, or be implemented as, executable computer program instructions stored on computer-readable storage media such as volatile or non-volatile memory capable of being retrieved and executed by a processor to provide operations for the computing devices 128A-N.

As shown in FIG. 1, the fitness tracking computing system 100 can include several computer servers and databases. For example, the fitness tracking computing system 100 can include one or more application servers 108, web servers 110, and/or any other type of servers. For convenience, only one application server 108 and one web server 110 are shown in FIG. 1, although it should be recognized that the disclosure is not so limited. The servers can cause content to be sent to the computing devices 128A-N in any number of formats, such as text-based messages, multimedia messages, email messages, smart phone notifications, web pages, and so forth. The servers 108 and 110 can comprise processors (e.g., CPUs), memory units (e.g., RAM, ROM), non-volatile storage systems (e.g., hard disk drive systems), etc. The servers 108 and 110 can utilize operating systems, such as Solaris, Linux, or Windows Server operating systems, for example.

The web server 110 can provide a graphical web user interface through which various users of the system can interact with the fitness tracking computing system 100. The web server 110 can accept requests, such as HTTP requests, from clients (such as via web browsers on the computing devices 128A-N), and serve the clients responses, such as HTTP responses, along with optional data content, such as web pages (e.g., HTML documents) and linked objects (such as images, video, and so forth).

The application server 108 can provide a user interface for users who do not communicate with the fitness tracking computing system 100 using a web browser. Such users can have special software installed on their computing devices 128A-N that allows them to communicate with the application server 108 via the network. Such software can be downloaded, for example, from the fitness tracking computing system 100, or other software application provider, over the network to such computing devices 128A-N.

A practitioner 114 is shown interacting with the fitness tracking computing system 100 via a computing device 116. The practitioner 114 can be a physical therapist, rehabilitative specialist, athletic trainer, or any other type of user that wishes to define and structure customized exercise protocols for one or more of the users 136A-N. The practitioner 114 can define personalized user-specific exercise protocols 118 for each of the users 136A-N. The exercise protocols 118 can be selected from a protocol library 119 and/or based on customized protocols 121. The protocol library 119 can include a listing of, for example, preset exercises and the practitioner 114 can select one or more of the preset exercises for inclusion in a particular user's exercise protocol. Additionally or alternatively, through the use of customized protocols 121 the practitioner 114 can provide the definitions for a particular protocol. By way of example, the practitioner 114 specify the exact relationships between joints (angles, distance, and alignment) and set a tolerance level for each, or otherwise structure or otherwise create a newly defined protocol. Such customized protocols 121 can define, for example, movement qualifications for completing the protocol on a per user basis. In any event, each of the personalized exercise protocols 118 can define, for example, types of exercises, number of repetitions, movement instructions, and so forth.

When the users 136A-N access the fitness tracking computing system 100 via their respective computing devices 128A-N, their customized exercise protocol 120A-N can be provided via the display 134. In accordance with various embodiments, one or more of the customized exercise protocol 120A-N can automatically evolve, adapt, or otherwise respond to the movement data collected from user performing the protocol. By way of example, upon detecting that a particular user 136A-N is having trouble completing the range of motion for a particular exercise, their customized exercise protocol can automatically be adjusted to provide them with an updated protocol that specifically addresses the detected deficiency. Upon successful completion of the updated protocol, the user can then again be presented with the original protocol. Their performance can again be monitored and a determination can be made as to whether additional updated protocol(s) should be provided to that particular user. Such monitoring, adjustments, and updating can happen in real-time, in an automated fashion. Additionally, on a global scale, the fitness tracking computing system 100 can track the success of various updated protocols in addressing user deficiencies, and based on that track, recommend specific updated protocols for specific users based on, for example, type of deficiency, user demographic, rehabilitation type, and so forth.

With regard to accessing an exercise protocol, in some embodiments, a user 136A-N can be provided with a one-time use web address to access a user-specific exercise protocol. When the user 136A-N navigates to the web address using a web browser on their computing device 129A-N, they can be presented with their customized exercise protocol 120A-N. Accessing the one-time use web address (sometimes referred to as a temporary URL) can assist in providing integration of a user's completion of certain exercise protocol's into their medical records, or otherwise allow the user data to easily be provided to appropriate entities for tracking. While one-time use web addresses are one example way to provide customized exercise protocols 120A-N to users, this disclosure is not so limited. In other embodiments, for example, users 136A-N can be provided with user accounts on the fitness tracking computing system 100. The users 136A-N can access their user accounts, such as via a web browser or a specialized application on their computing device 128A-N and access their customized exercise protocols 120A-N. The protocol (s) presented to the users 136A-N can be specially selected and/or designed for that particular user. Thus, instead of simply accessing a predetermined routine, the user can access a protocol that is customized for them. Further, in some embodiments, a user cannot necessarily advance the next protocol until satisfactory completion of the preceding protocol, both from a quantitative and qualitative perspective. In some embodiments, if it is determined that user is having trouble completing a particular protocol (i.e., due to range of motion issues), the fitness tracking computing system 100 can automatically select different protocols that are designed to target the particular areas in which the user needs to improve. In any event, once their protocols are accessed, instructions for various exercises can be provided to their computing device 129A-N. Such instructions can be provided, for example, as graphics, pictures, videos, written instructions, or combinations thereof.

As described in more detail below, the users 136A-N can position their computing devices 128A-N such that the camera 130 of the devices captures their movements. Based on the real-time video feed collected by the camera 130, real-time image processing motion tracking can be performed. In some embodiments, for example, wireframes 138A-N of the users 136A-N are generated based on the detected joint positions, although this disclosure is not so limited. Furthermore, the image processing and analytics can be performed by the computing devices 128A-N or the fitness tracking computing system 100. In some embodiments, some initial image processing can be performed locally by the computing devices 128A-N, with the remainder of the image processing performed by the fitness tracking computing system 100. In any event, movements of the users 136A-N can be tracked and compared to the instructed movements such that a determination can be made as to whether the users 136A-N are completing the protocol as defined.

User reporting 122A-N can be provided to the fitness tracking computing system 100 that provides, for example, verification a protocol was successfully performed. Additionally or alternatively, the reporting 122A-N can include other performance related metrics, such as exercise duration, range of motion data, and so forth. The reporting 123 can be provided to the practitioner 114 (or any of a variety of other recipients) via their computing device 116. Such reporting 123 can include, for example, analytics, compliance reports, and/or other insights and can allow for the viewing of key metrics over time for each user 136A-N.

The user reporting 122A-N can provide information to the fitness tracking computing system 100 which can be aggregated and analyzed at various levels, such as at a global level or a variety of other levels based on demographics, injury type, geography, and so forth. As such, the user reporting 122A-N can include a variety of information for each user 136A-N, such as geographic data, demographic data, compliance data, time/date data, movement data, and so forth. Using this data collected over time and from a wide array of users 136A-N, the fitness tracking computing system 100 can, for example, digitally track kinematic change of each user and compare such change across a plurality of other users. Such comparisons can be helpful in assessing, for example, a particular user's rehabilitation for an injury as compared to their cohorts. Such aggregated data can also be utilized, such as via machine learning processes, to accesses which exercises are the most effective over time. As is to be appreciated, a wide variety of other insights can be gleaned from the aggregated user reporting 122A-N.

While FIG. 1 shows the users 136A-N in separate remote locations 126A-N, it is to be appreciated that two or more of the user 136A-N can be physically within the same location. Furthermore, the practitioner 114 can also be physically present with one or more of the users 136A-N at the location where the exercise protocol is being completed. In some embodiments, video conferencing or other types of real-time communication, is facilitated by the fitness tracking computing system 100 between the practitioner 114 and the users 136A-N simultaneously the user is completing the exercise protocols. Thus, machine vision can be used to verify the particular movement of a user 136A-N concurrently with the provisioning of a live video conference with the practitioner 114.

Figure 2:
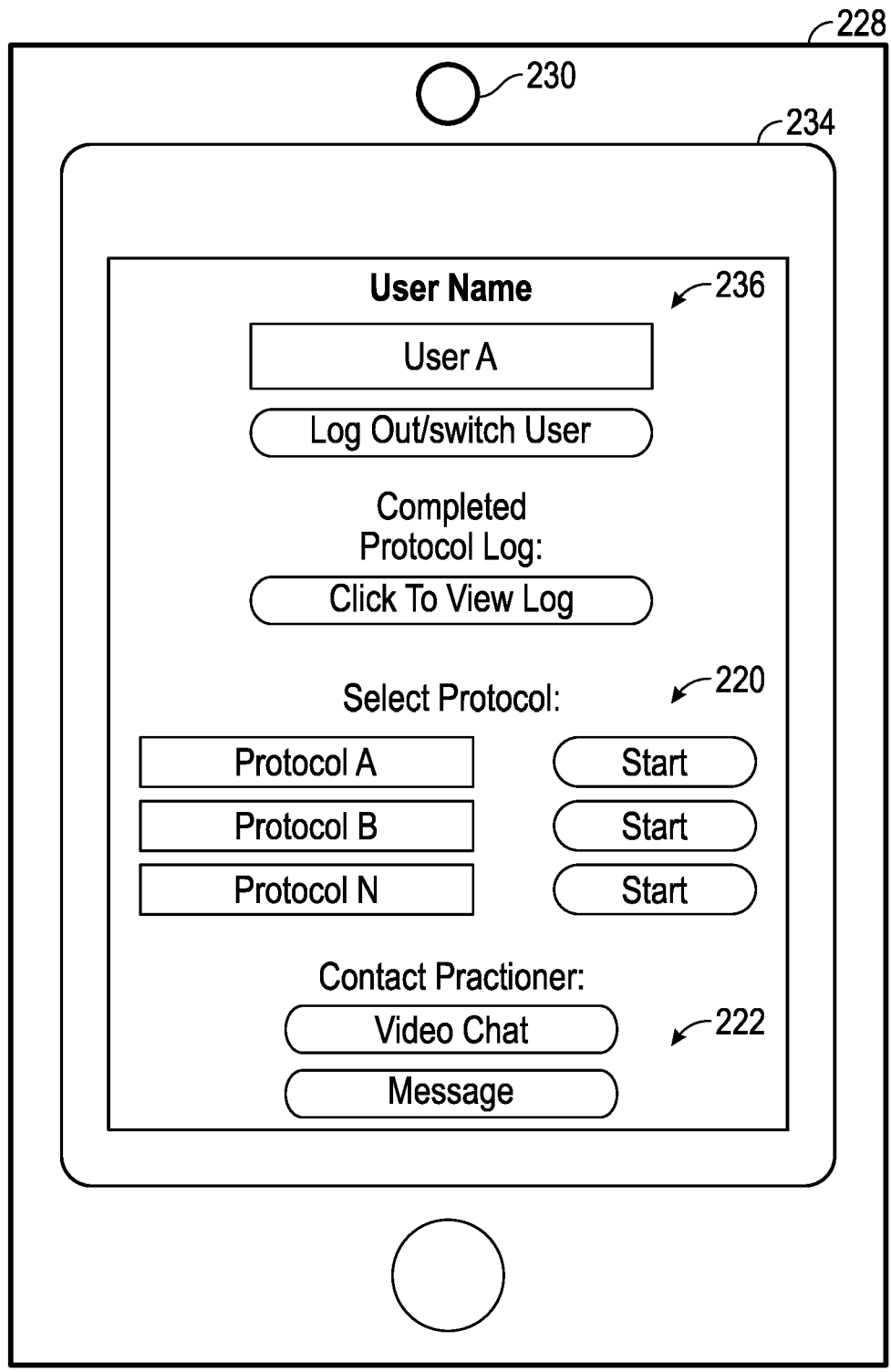
FIG. 2 schematically depicts an interface of an example computing device in accordance with one non-limiting embodiment.
Figure 3:
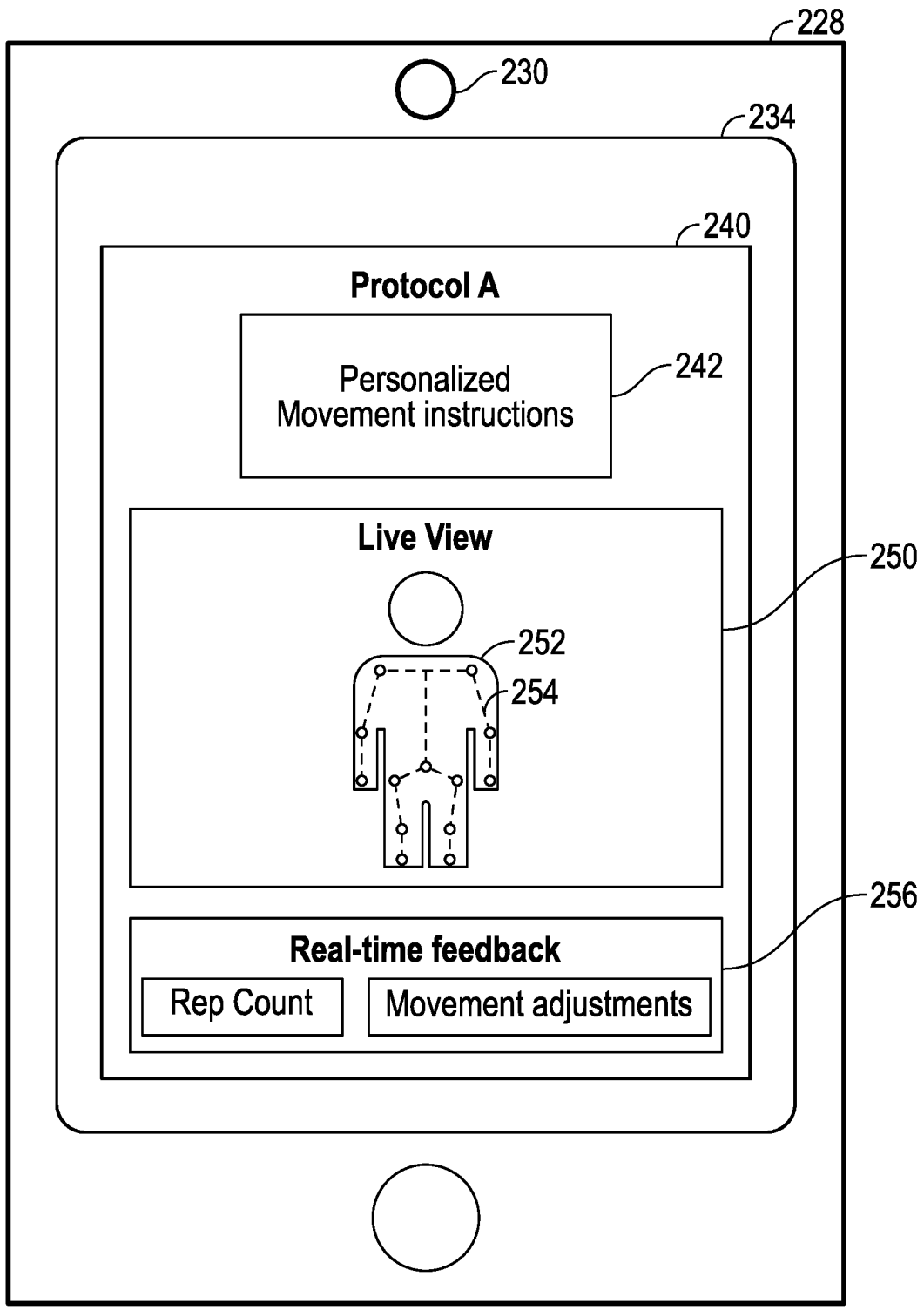
FIG. 3 schematically depicts an interface of an example computing device in accordance with one non-limiting embodiment.
Figure 4:
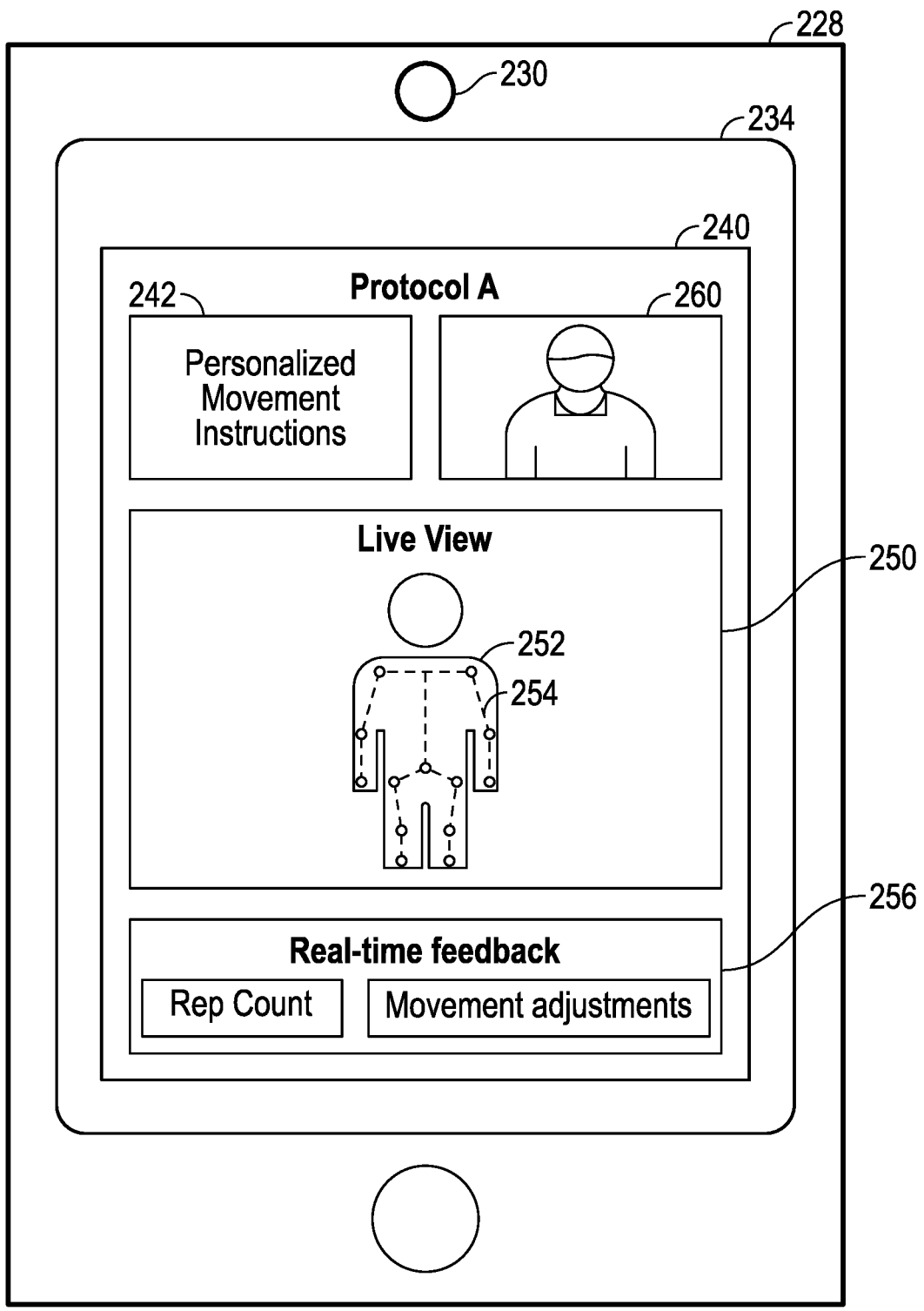
FIG. 4 schematically depicts an interface of an example computing device in accordance with one non-limiting embodiment.

FIGS. 2-4 schematically depict a simplified interface that can be presented on a user's computing device by a fitness tracking computing system in accordance with various embodiments. The interface can be provided, for example, through a web browser, a specialized application, or other suitable software exited by a computing device. Referring first to FIG. 2, a computing device 228 with a camera 230 and a display 234 is shown. The camera 230 can be "built-in" the computing device 228, as opposed to a specialized motion-tracking camera, for example. The display 234 can provide a home screen that allows a user to access various functionality, such as switch users, review previously completed exercise protocols, and so forth. In the illustrated example, the user is presented with a communication option 222 to contact a practitioner, such as via a video chat or a message. Additionally, in this example embodiment, a list of exercise protocols 220 are presented. As shown, the user has selected the first protocol in the list. Upon selection of the first protocol, the display 234 can present, for example, the exercise protocol 240, as schematically shown in FIG. 4. The exercise protocol 240 can be presented in any suitable format. In the illustrated example, personalized movement instructions 242 are present. Such instructions can be provided as graphics, photos, videos, written descriptions, or in any other suitable format.

In the illustrated example, a live view 250 is provided to the user so that an image 252 of the user (FIG. 3), as collected by the camera 230, is presented on the display 234. It is to be appreciated, however, that some embodiments may not necessarily provide an image 252 of the user on the display 234. The illustrated example also schematically displays a wire frame 254 of the user, as can be generated through image processing techniques. As provided above, the wire frame 254 can be utilized to track the movements of the user as they perform their personalized exercise treatment. While the wire frame 254 is shown graphically presented on the display 234 in FIG. 3, this disclosure is not so limited.

In this embodiments, the user is also provided with real-time feedback 256 via the display 234. Such real-time feedback 256 can include, without limitation, a repetition count, a timer, an exercise count, and so forth. Further, in some embodiments, the feedback 256 can include movement adjustments to aid the user in performing the exercise protocol. By way of example, the real-time feedback 256 may instruct the user to keep their back straight, bend their legs further, slow down, speed up, and so forth. In any event, such real-time feedback 256 can be based on the real-time track of the movements of the user in comparison to the personalized movement protocol they are performing.

FIG. 4 provides an example embodiment similar to FIGS. 2-3. In this embodiment, however, a live video chat window 260 can allow the user to have real-time communications with a third party, such as a healthcare provider, physical therapist, physical trainer, and so forth. In some embodiments, the third party can be viewing performance metrics of the user in real-time during the video chat, as provided to them by a fitness tracking computing system. As such, the third party can provide instruction or guidance, based on the user's real-time movements.

As is to be appreciated, a wide range of users can utilize the systems and methods described herein. As such, movements that are deemed to comply with certain exercise protocols or other movement protocols may vary based on the user. By way of example, a high performance athlete may need to perform certain movements with a high degree of precision and accuracy before the system deems they have complied with the protocol. An elderly user, however, may be permitted to perform the movements at a lower performance level, while still being deemed to have successfully completed the particular movement. In accordance with the systems and methods described herein, the healthcare professional or other user can define tolerance levels on a user-by-user basis and/or a movement-by-movement bases. Such tolerance customization is schematically shown in FIGS. 5-6.

Figure 5:
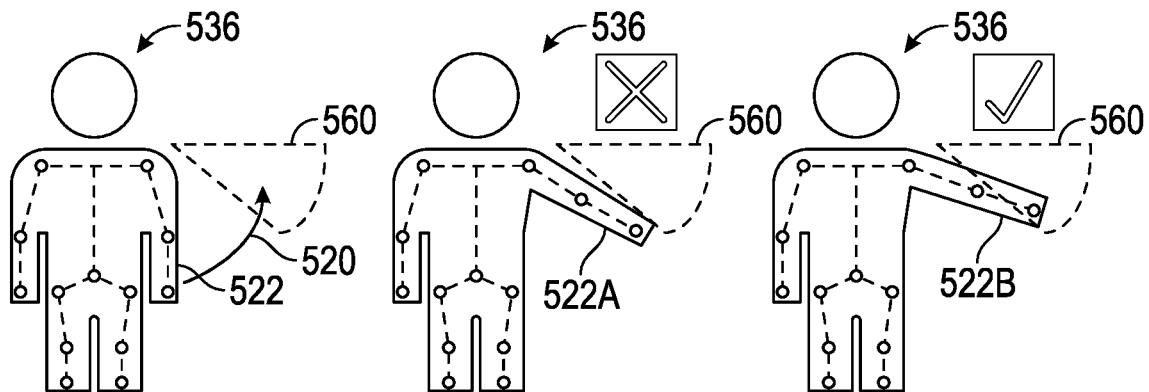
FIG. 5 schematically depicts the customization of movement compliance tolerance levels in accordance with one non-limiting embodiment.
Figure 6:
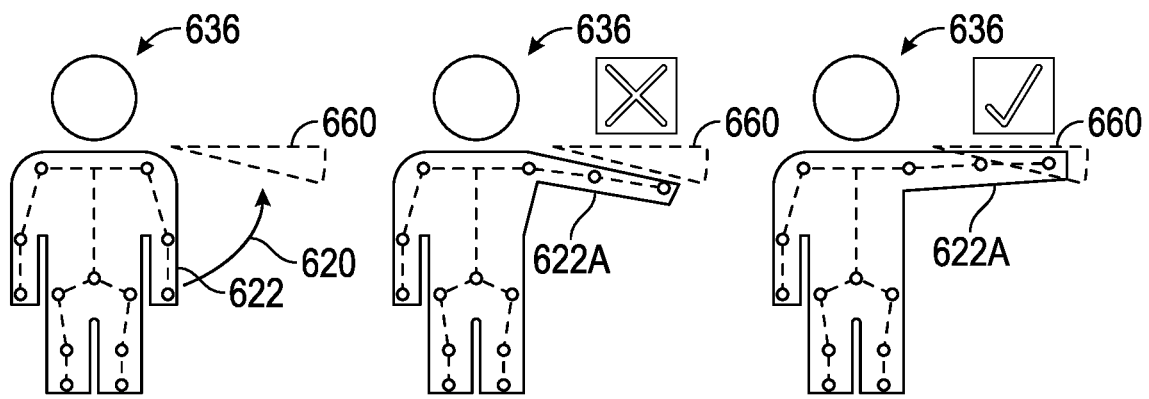
FIG. 6 schematically depicts the customization of movement compliance tolerance levels in accordance with one non-limiting embodiment.

Referring to FIGS. 5-6, a user 536 (FIG. 5) and has been instructed to lift their arm 522 in the direction indicated by arrow 520 until their arm 522 is perpendicular to the ground, and a user 636 (FIG. 6) has also been instructed to lift their arm 622 in the direction indicated by arrow 620 until their arm 622 is perpendicular to the ground. A tolerance window 560 is schematically shown in FIG. 5 and a tighter tolerance window 660 is schematically shown in FIG. 6. As such, the user 636 is being held to a higher performance standard.

The user 536 first raises their arm 522A to a position that is beneath the tolerance window 560. As such, that movement does not count toward completing their movement protocol. Once user 536 raises their arm 522B to within the tolerance window 560, the movement is counted as successfully completing the movement.

Looking now at the user 636 in FIG. 6, their arm 622A is first raised to a position that is beneath the tolerance window 660, yet is above the movement performed by the user 536. Nevertheless, due to the tighter tolerance window 660, the movement does not count toward completing their movement protocol. Once user 636 raises their arm 622B to within the tolerance window 660, the movement is counted as successfully completing the movement.

While FIGS. 5-6 depict a tolerance window used to monitor simple arm lift, it is to be appreciated that customizable tolerance windows of various formats can be used across a wide variety of movements, exercises, and performance metrics. Thus, the tolerance window does not need to necessarily relate to angular motion, but instead can be used to allow for performance tracking of a variety of different movement types.

Figure 7:
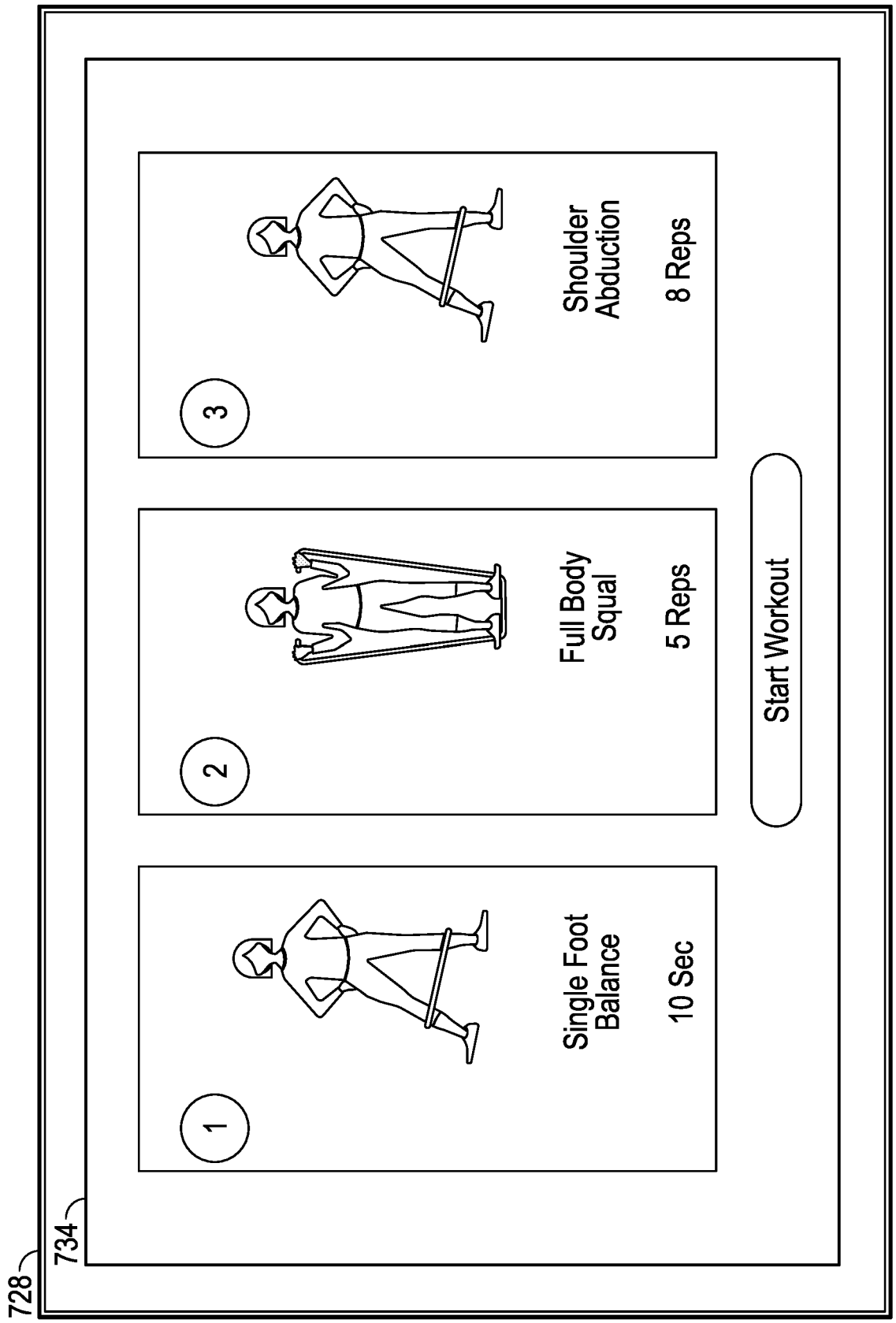
FIG. 7 schematically depicts an interface of an example computing device in accordance with one non-limiting embodiment.
Figure 8:
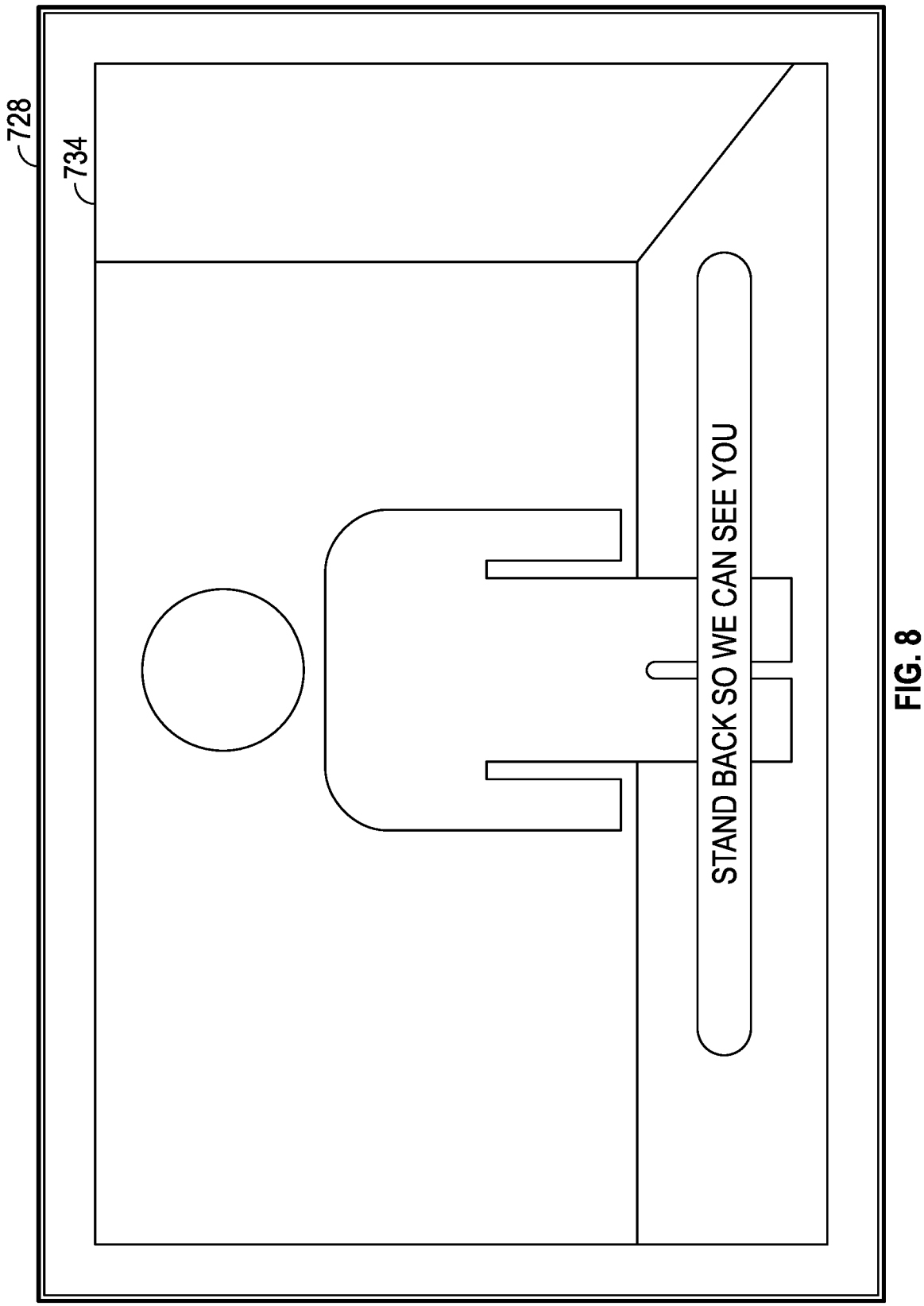
FIG. 8 schematically depicts an interface of an example computing device in accordance with one non-limiting embodiment.
Figure 9:
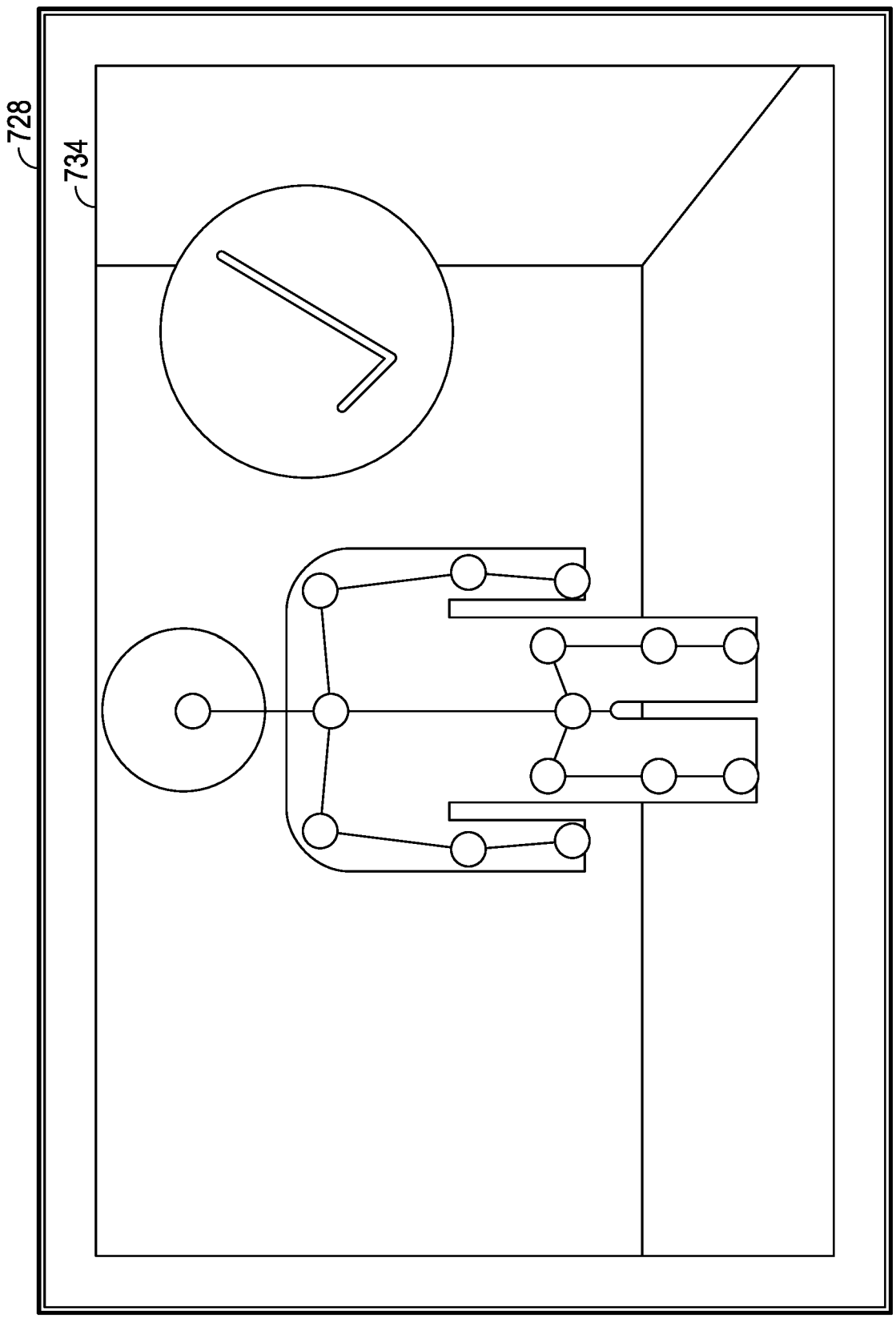
FIG. 9 schematically depicts an interface of an example computing device in accordance with one non-limiting embodiment.
Figure 10:
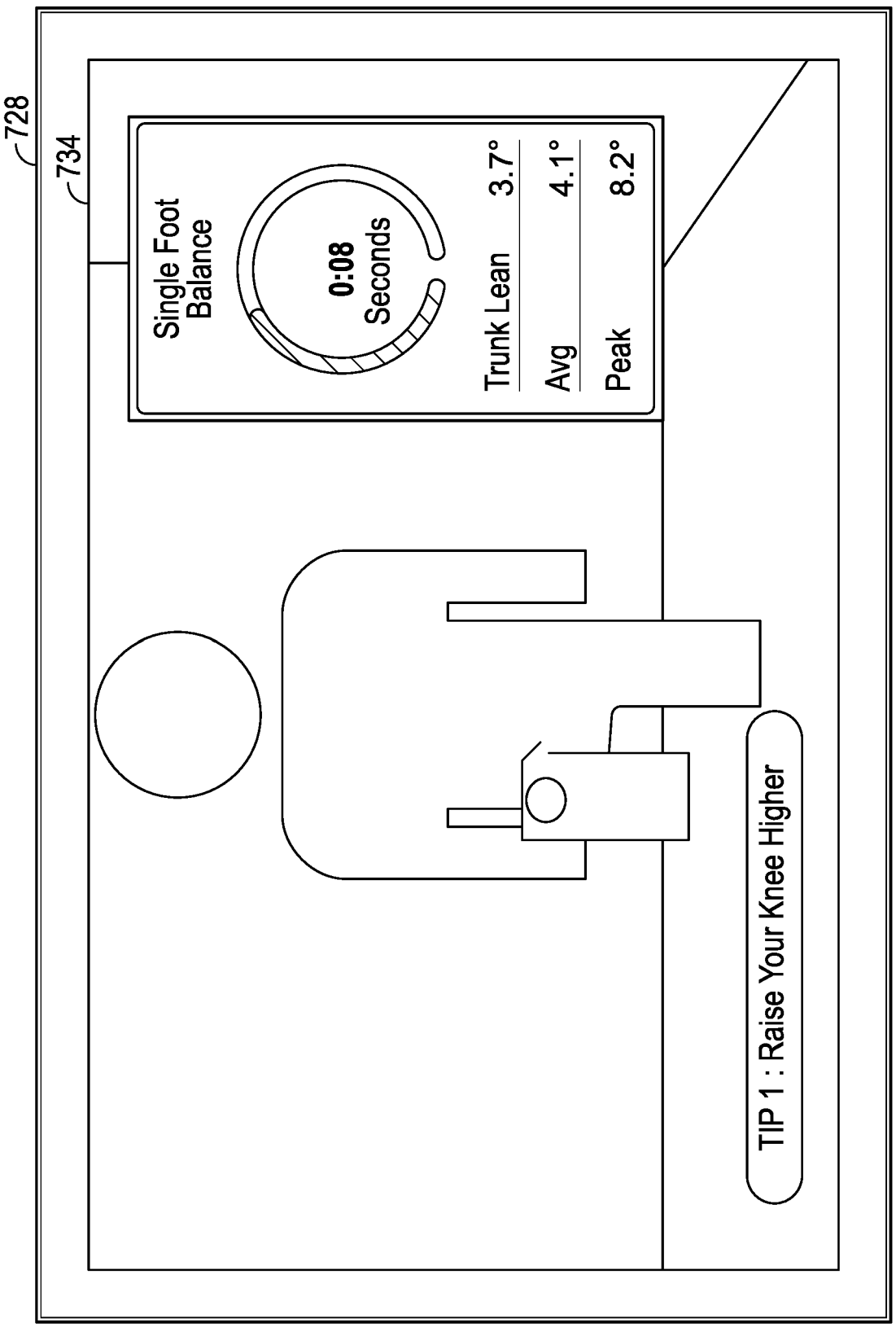
FIG. 10 schematically depicts an interface of an example computing device in accordance with one non-limiting embodiment.
Figure 11:
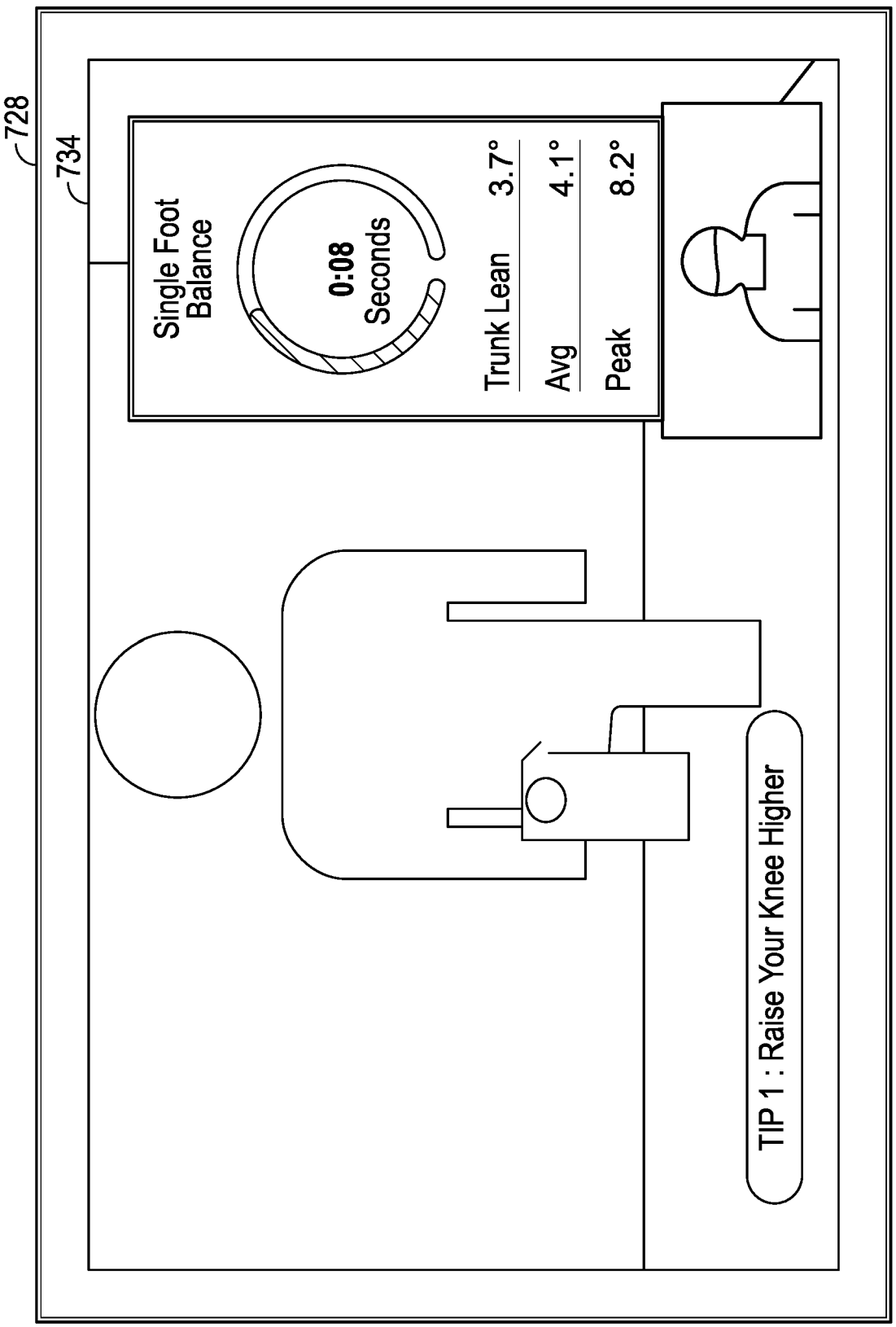
FIG. 11 schematically depicts an interface of an example computing device in accordance with one non-limiting embodiment.

FIGS. 7-11 depicts a series of example user interfaces that can be presented on a computing device 728. The computing device 728 can be similar to any of computing devices 128A-N and 228, for example. Referring first to FIG. 7, the user interface 734 can provide an overview of a workout that has been assigned to, delivered, or otherwise provided to the user of the computing device 728. Upon starting the workout, FIG. 8 depicts the user interface 734 during a video calibration step. During this step, the user's relative placement to the computing device 728 can be checked to ensure that the machine vision processing will properly function, for example. Example embodiments of these operations are depicted below with regard to FIGS. 19-40. FIG. 9 schematically illustrates a successful video calibration, as joints of the user are highlighted. FIG. 10 depicts the execution of an exercise protocol, shown as a timed Single Foot Balance protocol. As shown in FIG. 10, through machine vision processing, the technique of the user can be assessed to determine whether the movements of the user qualifies for completion of the exercise protocol. Real-time analytics can be presented to the user on the user interface 734, such as, for example, trunk lean degree, average trunk lean degree, peak lean degree, and so forth. As it to be appreciated, the particular real-time analytics presented to the user, if any, can depend on the particular exercise protocol being performed. Finally, FIG. 11 depicts a real-time video chat between the user and a practitioner. Thus, the movements of the user can be verified simultaneously as a live video chat is being conducted with the practitioner.

While FIGS. 7-11 depict a series of example user interfaces that can be presented on a computing device incorporating a live video feed of the user, other embodiments can utilize other types of user interfaces. FIGS. 12-15 depict other example interfaces that provide real-time biomechanical visualizations to a user. In these example embodiments, instead of presenting a live video feed of the user, a simplified animated graphic is used to provide real-time visual feedback to a user that is correlated to the user's physical movements. Further, while FIGS. 12-15 provide examples of various biomechanical visualizations, it is to be appreciated that a variety of different types of biomechanical visualizations can be utilized without departing from the scope of the present disclosure. Furthermore, the relative complexity of the biomechanical visualizations can vary based on user. A geriatric user can be presented with a relatively simple biomechanical visualization, while a performance athlete can be presented with a more complex and sophisticated biomechanical visualization, for example.

Figure 12:
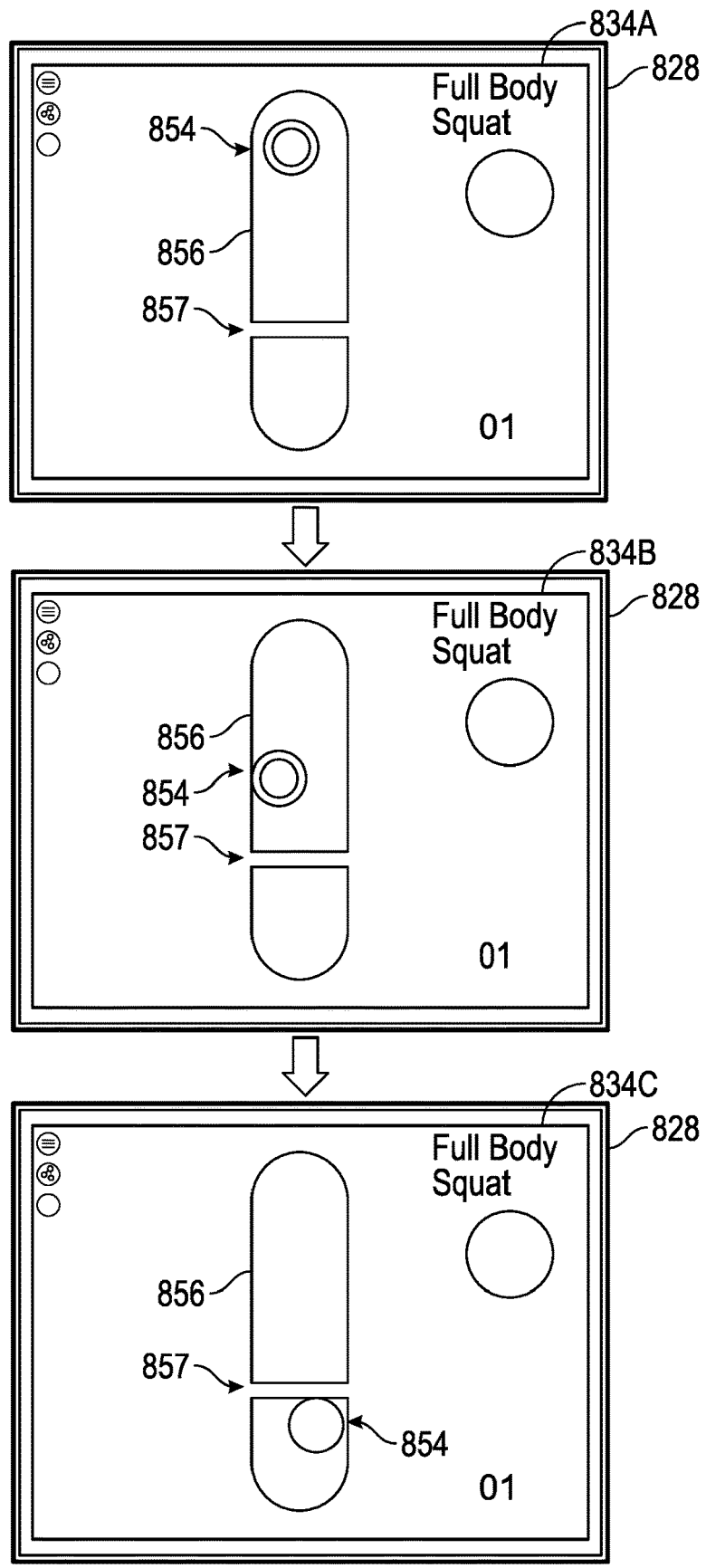
FIG. 12 schematically depicts the progression of an interface of an example computing device in accordance with one non-limiting embodiment.

Referring first to FIG. 12, an animation of an example user interface 834A-C over time is shown on a computing device 828. The user interface 834A-C depicts a movement tolerance graphic 856 that is correlated to a particular movement. As is to be appreciated, the relative size and shape of the movement tolerance graphic 856 can vary based on the particular movement being performed and the associated tolerance level for the user. In the example embodiment, the user interface 834A-C also includes a movement reference indicator 857. While the movement tolerance graphic 857 is horizontal line toward the bottom of a downward stroke in FIG. 12, it is to be appreciated that the type, location, and format of the movement reference indicator 857 can be based on the particular movement being tracked. Also provided on the user interface 834A-C is an example real-time biometric marker 854. The position and movement of the movement tolerance graphic 854 can be based on machine vision techniques, as described above. The real-time biometric marker 854 can be correlated directly to a particular joint of the user, or other body part or location on the user. In any event, as the user completes a particular move (shown as a squat in FIG. 12), the user's movement can be translated to the user interface 834A-C by the real-time biometric marker 854. In this embodiment, the user is maintain the real-time biometric marker 854 within the bounds of the movement tolerance graphic 856 during the entire stroke of the movement. The user interface 834A depicts the user at the beginning of the movement, user interface 834B depicts the user during the movement, and user interface 834C depicts the user at the bottom of the movement. In this case, the real-time biometric marker 854 can be correlated, for example, to the hips of the user during the full body squat movement. As the user is performing the movement, the user can watch the corresponding movement of the real-time biometric marker 854 in real-time and try to keep the marker within the border of the movement tolerance graphic 856.

In some embodiments, completion of a particular movement can result in a graphical change to the real-time biometric marker 854. For example, once the user reaches the bottom of the stroke for a particular movement, the real-time biometric marker 854 can change colors, size, and or shape. As shown by user interface 834C, as the real-time biometric marker 854 has crossed over the movement reference indicator 857, the real-time biometric marker 854 has graphically changed to provide visual feedback to the user. The real-time biometric marker 854 can then revert to its original form upon the user returning to the top of the stroke, or at least cross back over the movement reference indicator 857. Further, beyond the real-time biometric marker 854 and the movement tolerance graphic 856, the user interface 834A-C can also present additional information to the user, such as a repetition count, a timer, a skeletal overlay, a live video feed, and so forth.

Figure 13:
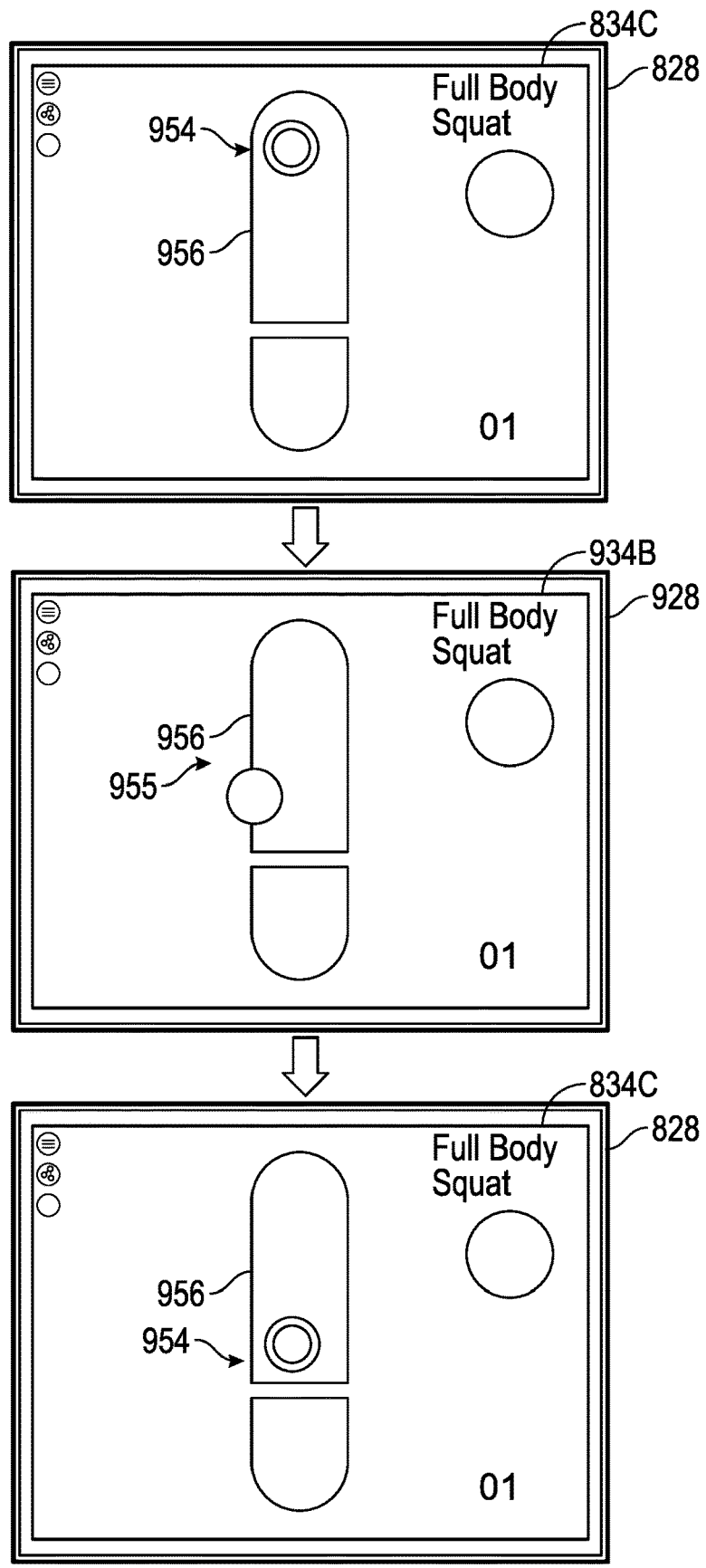
FIG. 13 schematically depicts the progression of an interface of an example computing device in accordance with one non-limiting embodiment.

Referring now to FIG. 13. an animation of an example graphical interface 934A-C on a computing device 928 that is similar to the graphical interface of FIG. 12 is depicted that shows the location of a real-time biometric marker 954 relative to an example movement tolerance graphic 956. The user interface 934A depicts the user at the beginning of the movement and user interface 934B depicts the user during the attempted completion of movement. In this example, the user has failed to comply with the tolerance level for the movement during the downward stroke. As such, the real-time biometric marker 954 is graphically changed to a secondary real-time biometric marker 955 to provide real-time visual feedback of the deviation to the user, as shown in user interface 934B. The form of the secondary real-time biometric marker 955 can vary, but in some embodiments, the secondary real-time biometric marker 955 is a different color, shape, and/or opacity as the real-time biometric marker 954. The change to the secondary real-time biometric marker 955 can also be accompanying by an audio alert. Once the user corrects the deviation, the original real-time biometric marker 954 can be displayed, as shown in user interface 934C.

Figure 14:
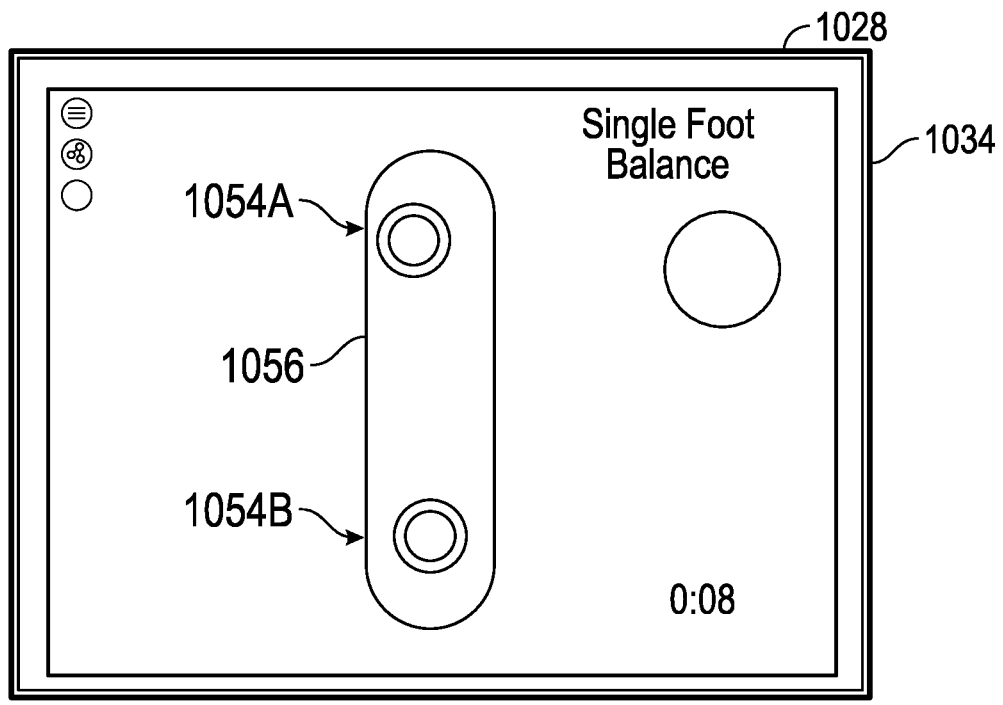
FIG. 14 schematically depicts an interface of an example computing device in accordance with one non-limiting embodiment.

Furthermore, while FIGS. 12 and 13 depict the presentation of a single real-time biometric marker, this disclosure is not so limited, as any suitable number of real-time biometric markers can be presented to a user for a particular movement. FIG. 14, for example, depicts an example user interface 1034 that is presented on a computing device 1028 and has a first real-time biometric marker 1054A and a second real-time biometric marker 1054B. In this example embodiment, the user is being instructed to stand on a single foot for a time period such that both real-time biometric marker 1054A-B remain essentially vertically aligned and inside a movement tolerance graphic 1056. As is to be appreciated, if one or both of the real-time biometric marker 1054A-B do not stay within the movement tolerance graphic 1056, secondary real-time biometric markers can be displayed to the user until the user corrects the deviation.

Figure 15:
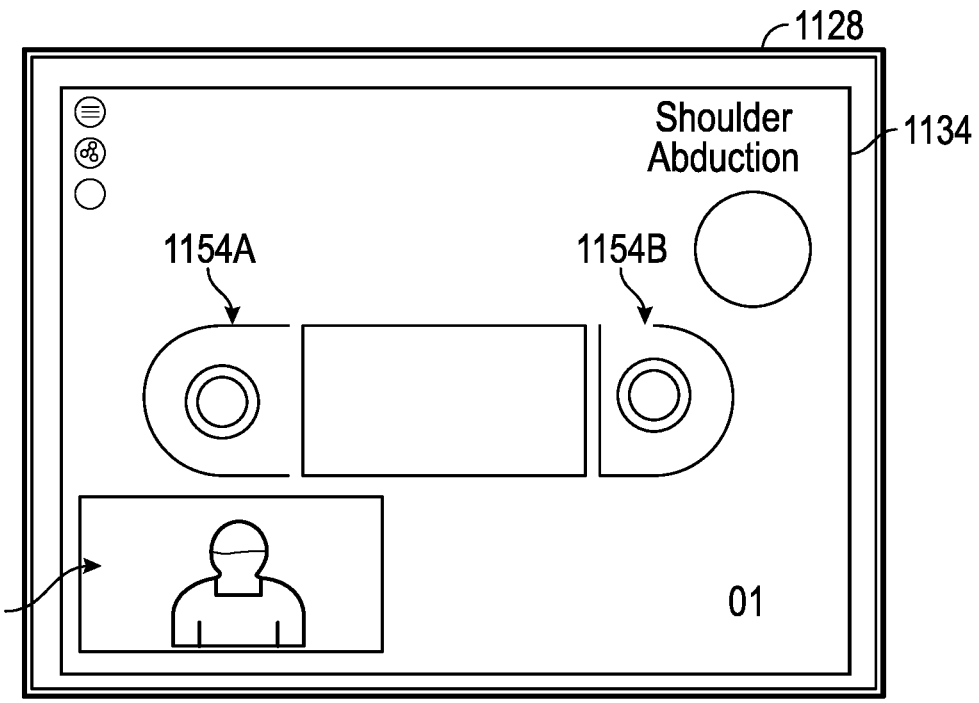
FIG. 15 schematically depicts an interface of an example computing device in accordance with one non-limiting embodiment.

FIG. 15 depicts yet another example user interface 1134 that can be presented on a computing device 1128. Similar to FIG. 14, this interface has a first real-time biometric marker 1154A and a second real-time biometric marker 1154B that are each to remain inside a movement tolerance graphic 1156 during an instructed movement. As shown, a live video chat window 1160 is also presented on user interface 1134. The live video chat window 1160 can allow the user to have real-time communications with a third party, such as a healthcare provider, physical therapist, physical trainer, and so forth. In some embodiments, the third party can be viewing performance metrics of the user in real-time during the video chat, as provided to them by a fitness tracking computing system. As such, the third party can provide instruction or guidance, based on the user's real-time movements.

As provided above, the systems and methods described herein can beneficially leverage a user's computing device for data collection without requiring the user to install specialized hardware (such as a specialized motion sensing/depth sensing camera system). In fact, in some embodiments, the functionality of the systems described herein can be accessed simply through a web browser executing on a user's computing device. As is to be appreciated, however, a wide variety of computing devices may be utilized by users when accessing the system. Some users may prefer laptop computers with either a built-in camera or use a conventional USB-based web camera peripheral device, while others may use tablet computers or a mobile computing device, such as a smart phone, while others may use a smart TV or gaming system. Each of these computing devices may have a different screen size, different types of camera, and the video feed from the cameras may have different frame rates or other operational parameters.

Figure 16:
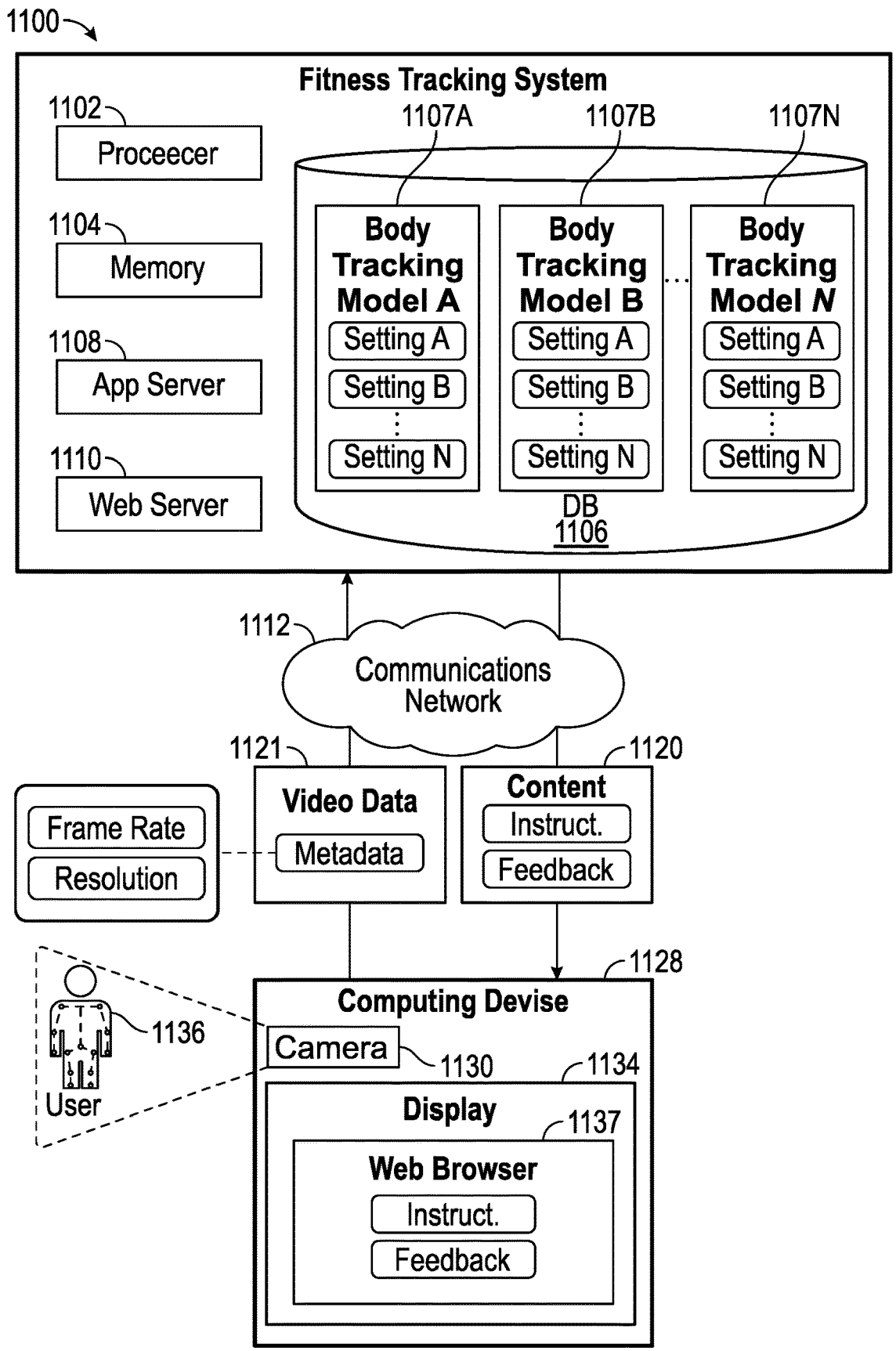
FIG. 16 schematically depicts a fitness tracking computing system facilitating remote exercise sessions based on detected operational parameters of a remote computing device.

FIG. 16 schematically illustrates an example fitness tracking computing system 1100 responsively adapting to the operational characteristics of a computing device 1128 of a user 1136. Similar to FIG. 1, fitness tracking computing system 1100 can include, for example, a processor 1102, a memory 1104, an app server 1108, and a web server 1110, although this disclosure is not so limited. As schematically shown, the fitness tracking computing system 1100 can also include one or more databases 1106 that store one or more body tracking models 1107A-N. It is to be appreciated that FIG. 16 is simply a schematic representation of the fitness tracking computing system 1100 and the storage of the associated body tracking models 1107A-N may be local, remote, or combinations thereof. Moreover, embodiments of the fitness tracking computing system 1100, and other embodiments of the fitness tracking computing system described herein, can also be implemented in cloud computing environments. "Cloud computing" may be defined as a model for enabling ubiquitous, convenient, on-demand network access to a shared pool of configurable computing resources (e.g., networks, servers, storage, applications, and services) that can be rapidly provisioned via virtualization and released with minimal management effort or service provider interaction, and then scaled accordingly. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

The computing device 1128 of FIG. 16 is schematically shown to include a camera 1130, which can be, for example, a built-in web camera or conventional third party web camera that can be connected to the computing device 1128 via a USB connection, for example. The camera 1130 in FIG. 16 is not a specialized camera that is specially configured to work with the fitness tracking computing system 1100. The computing device 1128 in FIG. 16 also has a display 1134. The computing device 1128 is also shown to be executing a conventional web browser application 1137 that is navigated to a website address associated with the fitness tracking computing system 1100 through a communications network 1112. The display 1134 can show content 1120 via the web browser 1134, as provided by the fitness tracking computing system 1100, and described above. The resolution of the display 1134 can vary based on the type and size of device. The resolution of an example smart phone computing device display 1134 may be 750×1334 pixels, while the resolution of an example laptop computing device display 1134 may be 1920×1080 pixels.

Upon the computing device 1128 communicating with the fitness tracking computing system 1100, the fitness tracking computing system 1100 can determine the operational characteristics of the computing device 1128 and responsively adapt its image processing approach based on those characteristics. In the example embodiment shown in FIG. 16, the fitness tracking computing system 1100 can analyze the video data 1121 received from the computing device 1128. The video data 1121 can include metadata that provides technical data to the fitness tracking computing system 1100 for analysis. As shown, the metadata can indicate to the fitness tracking computing system 1100 the resolution of the display 1134 and the frame rate of the camera 1130. The frame rate can be, for example, in the rage of 15 to 60 frame per second (FPS). Notably, the video data 1121 can be collected when the user 1132 accesses the web page on the web browser 1134 (and gives permission to access the camera 1130, if needed) and be monitored through the user's session.

In accordance with some embodiments, when performing movement tracking and analysis, the fitness tracking computing system 1100 can utilize any of a number of the body tracking models 1107A-N, each having a number of adjustable parameters, for joint detection. The selection of the body tracking model and the adjustment of one or more of the parameters can occur in real-time by the fitness tracking computing system 1100 based on the video data 1121. In one embodiment, the frame rate is utilized to decide which of the body tracking models 1107A-N would likely perform the best. The frame rate can also be utilized to determine adjustments to the settings within that selected body tracking model. Generally, the fitness tracking computing system 1100 is seeking to balance latency and accuracy, given the operational parameters of the computing device 1128. The resolution information can be used by the fitness tracking computing system 1100 to determine the optimal presentation of the website content 1120 based on screen size.

Video scale factor is example setting of a selected body tracking model that can be automatically adjusted in real-time is a video scale factor. In some embodiments, the video scale factor is adjusted to arrive at a FPS rate of greater than 20. Another example setting is buffer length. It is noted that not all of the body tracking models 1107A-N necessarily allow for adjustment of video scale factors and/or buffer length. Nevertheless, in accordance with the systems and methods described herein, one or more settings of the selected body tracking models 1107A-N can be auto adjusted in real-time by the fitness tracking computing system 1100 to optimize the user experience.

Figure 17:
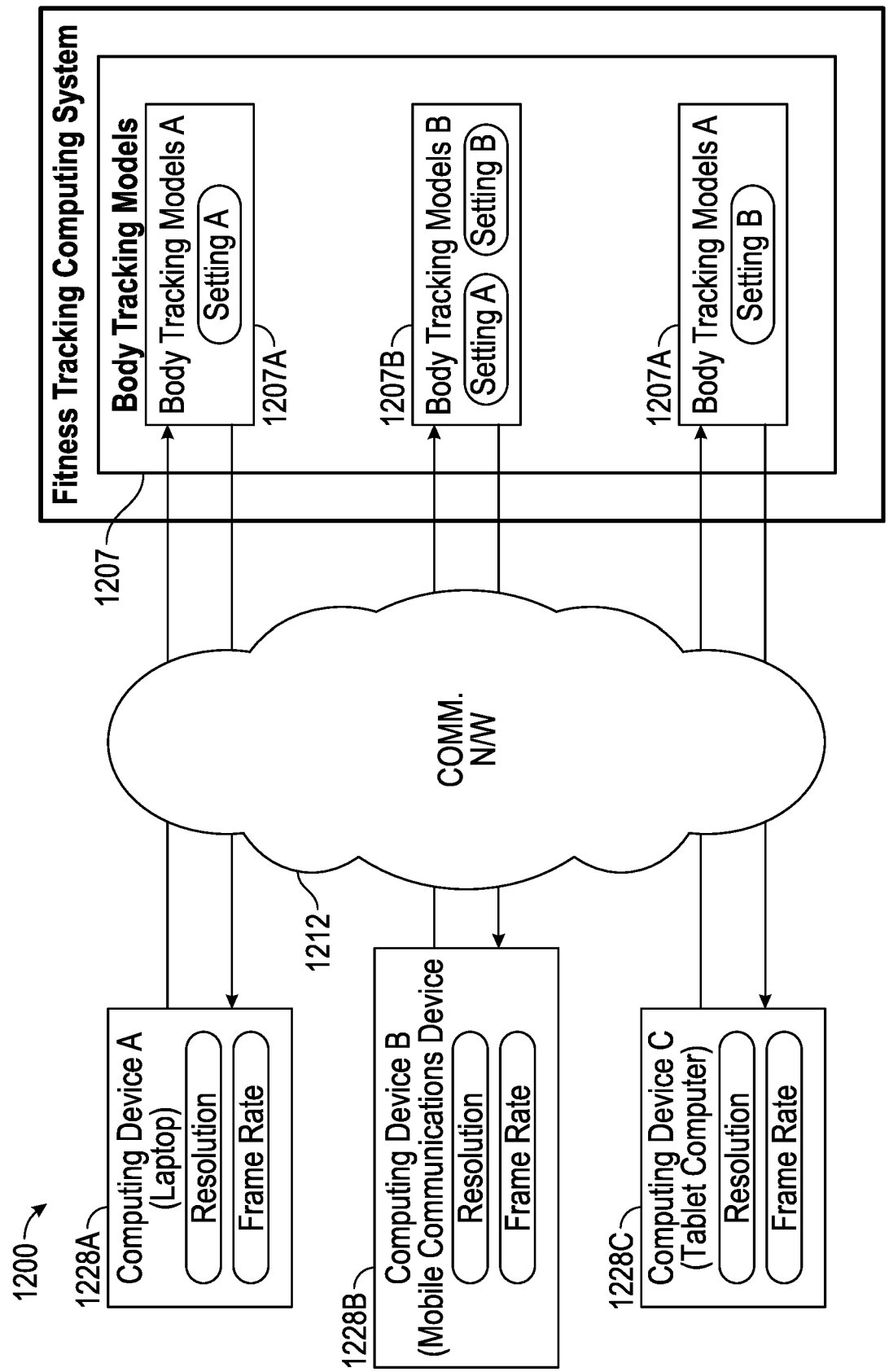
FIG. 17 schematically depicts a fitness tracking computing system providing remote exercise sessions to a plurality of different types of remote computing devices.

FIG. 17 schematically illustrates that a number of different type of computing devices 1227A-C can connect to a fitness tracking computing system 1200 in accordance with the present disclosure. The computing device 1228A is a laptop computer having a particular resolution and frame rate, the computing device 1228B is a mobile communications device having a different resolution and frame rate, and the computing device 1228C is a table computer having yet a different resolution and frame rate. Each of the computing devices 1228A-N can connect to the fitness tracking computing system 1200 through a communications network 1212. The fitness tracking computing system 1200 can utilize any of plurality of different body tracking models 1207, based on the operational parameters of the computing devices 1228A-N. For the purposes of illustration, a body tracking model A 1207A is being used to track the movements of a user associated with the computing device 1228A. Based the operational parameters of the computing device 1228A, the fitness tracking computing system 1200 has adjusted setting A of the body tracking model accordingly. A body tracking model B 1207B is being used to track the movements of a user associated with the computing device 1228B. Based the operational parameters of the computing device 1228B, the fitness tracking computing system 1200 has adjusted setting B of the body tracking model accordingly. The body tracking model A 1207A is also being used to track the movements of a user associated with the computing device 1228C. Based the operational parameters of the computing device 1228C, however, the fitness tracking computing system 1200 has adjusted setting B of the body tracking model.

Figure 18:
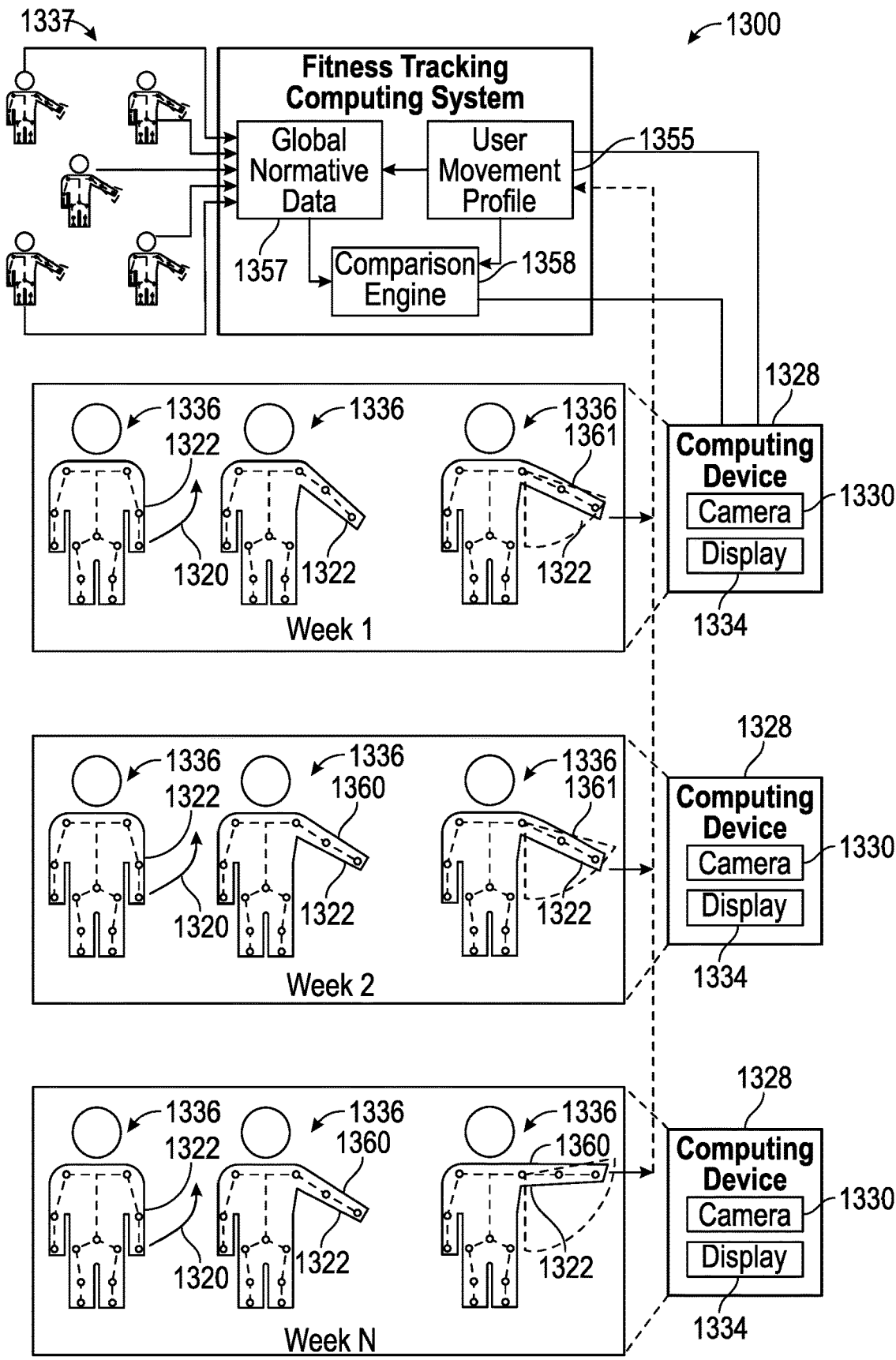
FIG. 18 schematically depicts a fitness tracking computing system generating a movement profile over time.

Referring now to FIG. 18, a fitness tracking computing system 1300 generating a movement profile of a user 1336 over time (i.e., Week 1 to Week N) is schematically depicted. For the sake of illustration, the movement profile is based on a lateral arm raise. As is to be readily appreciated however, a wide variety of movement profiles with varying levels of complexity can be generated in accordance with the presently disclosed systems and methods. In the illustrated example, the user 1336 is instructed through a display 1334 of their computing device 1328 to lift their arm 1322 in the direction indicated by arrow 1320 to detect range of motion. The motion of their arm 1332 is captured by a camera 1330 of their computing device 1328 and tracked by the fitness tracking computing system 1300. The timestamped range of motion 1361 can be stored by the fitness tracking computing system 1300 in a movement profile 1355 associated with that user 1332. As shown in the example illustration, the range of motion 1361 of the user 1336 improves over time, with the improvement being detected by the fitness tracking computing system 1300.

Along with the range of motion 1361, the fitness tracking computing system 1300 can track the demographics of the user 1336, a rate of improvement, among a wide array of other metrics and data. Additionally, a comparison engine 1358 of the fitness tracking computing system 1300 can compare the range of motion 1361 to global normative data 1357 that was collected over time from a plurality of users 1337. Such comparison can be used to determine if, for example, the rate of recovery for the user 1336 subsequent to a surgery is above or below a standard recovery progression. Thus, if user 1336 is a 55 year old female that recently had shoulder surgery, the progression of her range of motion 1361 can be compared to other 55 year old females that previously had the same surgery. Moreover, using insights from the global normative data, a wide variety of other determinations can be generated. For example, rates of progression can be cross-linked to the type of exercises performed, the time of the exercises where performed, the duration of each exercise session, and so forth, based on learnings from the global normative data 1357 aggregated by the fitness tracking computing system 1300.

As various systems and methods in accordance with the present disclosure can leverage an existing camera associated with a user's computing device, ensuring that the user is properly oriented relative to the camera can be essential for proper body movement tracking and quantification. Furthermore, the particular orientation of the user relative to the camera can vary based on the customized exercise protocol for that particular user. By way of example, a first exercise may require the user to squarely face the camera, a second exercise may require the user to face to their body to the right, a third exercise may require the user to sit in a chair facing to the left, and so forth. In accordance with the present disclosure, based on the customized exercise protocol for the user, a fitness tracking computing system can provide real-time instructions to the user via their computing device and measure and detect compliance with the instructions to ensure the user is properly positioned relative to the camera. Such approach can help to ensure the body tracking models and other machine vision techniques utilized by the fitness tracking computing system can properly monitor and quantify the user's movements while performing various exercises.

In accordance with various embodiments, when a user first engages with the fitness tracking computing system via their user device, the user may be instructed to step back away from the camera such that their whole body can be seen by the camera and they have adequate space to perform the exercise. Once their whole body is in view, specific orientation instructions can be provided to instruct the user to face a particular direction and the user's direction can be detected by the fitness tracking computing system in real-time to confirm compliance. Use body position can also be instructed (such as standing, seated, laying, and so forth) and the user's position can be detected by the fitness tracking computing system in real-time to confirm compliance. Once the user's position has been verified, the user can receive instruction regarding the exercise to be completed. While the user is moving in accordance with the instructions, the fitness tracking computing system can track and measure joints, for example, of the user and after one or more certain joints crosses a predetermined range of motion a repetition counter can be updated.

FIGS. 19-40 depict an example interface 1434 of an example user computing device 1428 during an example exercise session. The user computing device 1428 includes an on-board camera 1430, which can be, for example, a conventional front-facing camera, although this disclosure is not so limited. A real-time image of the user 1452, as collected by the camera 1430, can be presented on the interface 1434.

Figure 19:
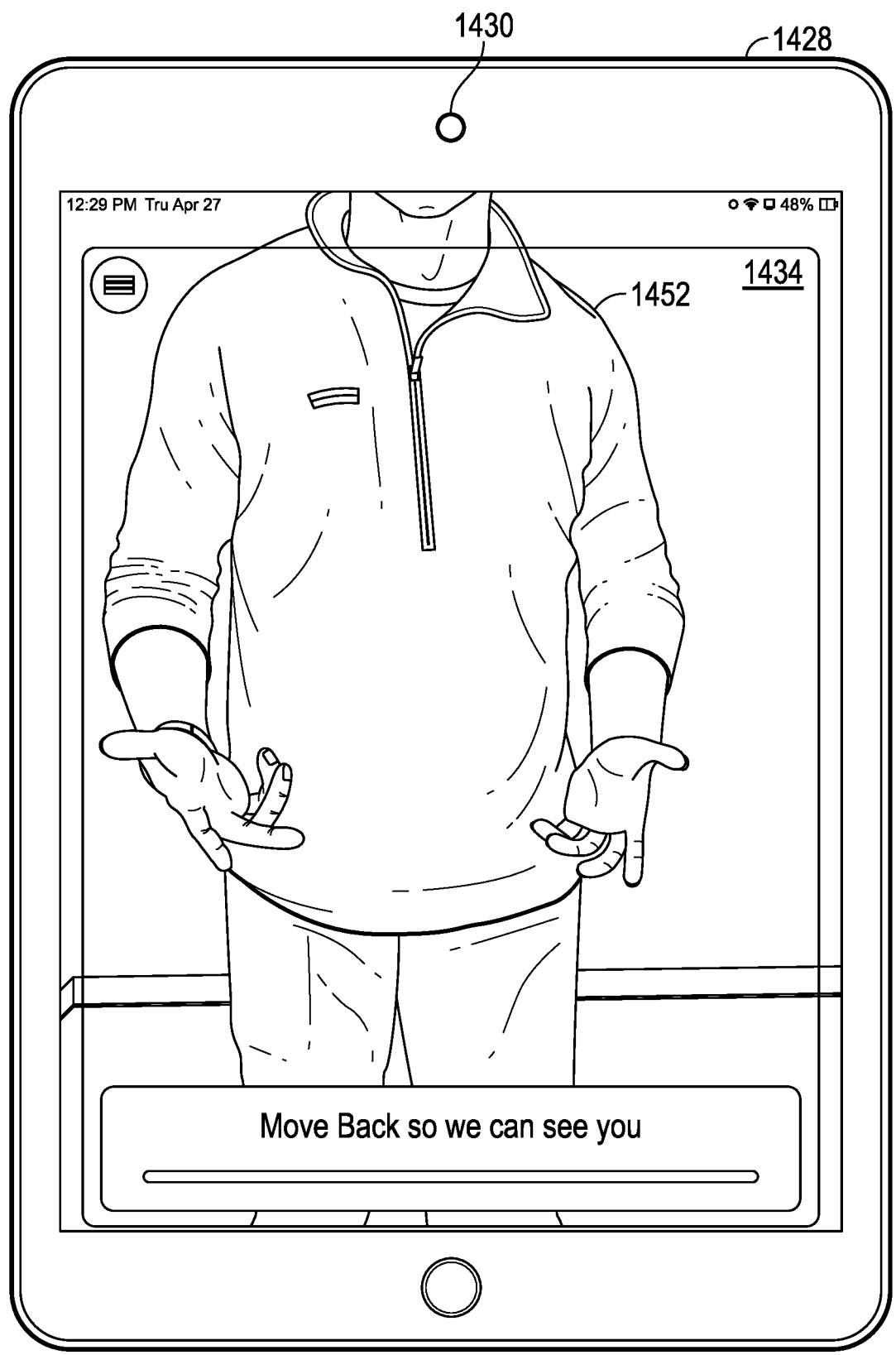
FIG. 19 depicts an example interface on a user computing device during an example exercise session.
Figure 20:
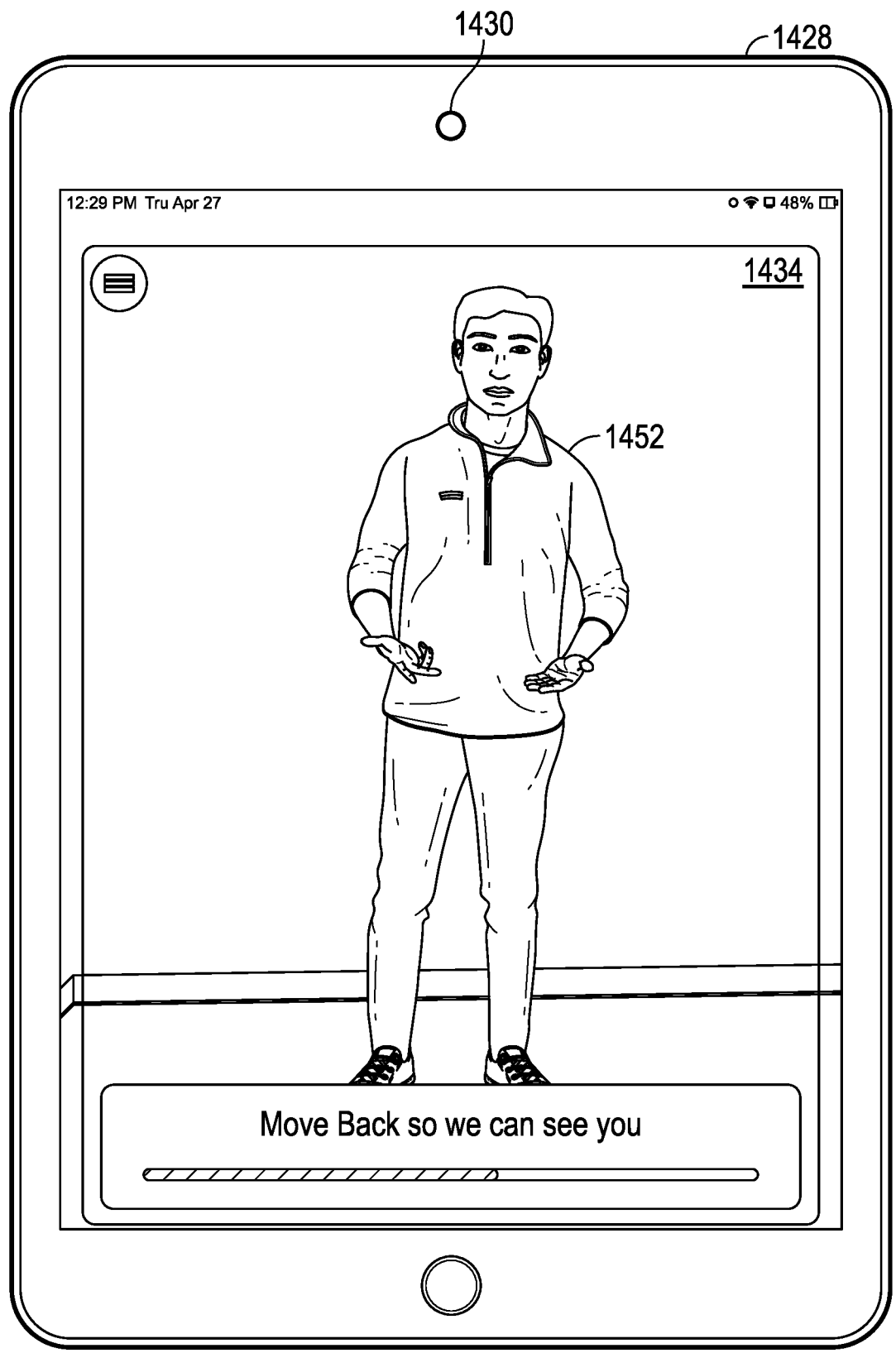
FIG. 20 depicts an example interface on a user computing device during an example exercise session.
Figure 21:
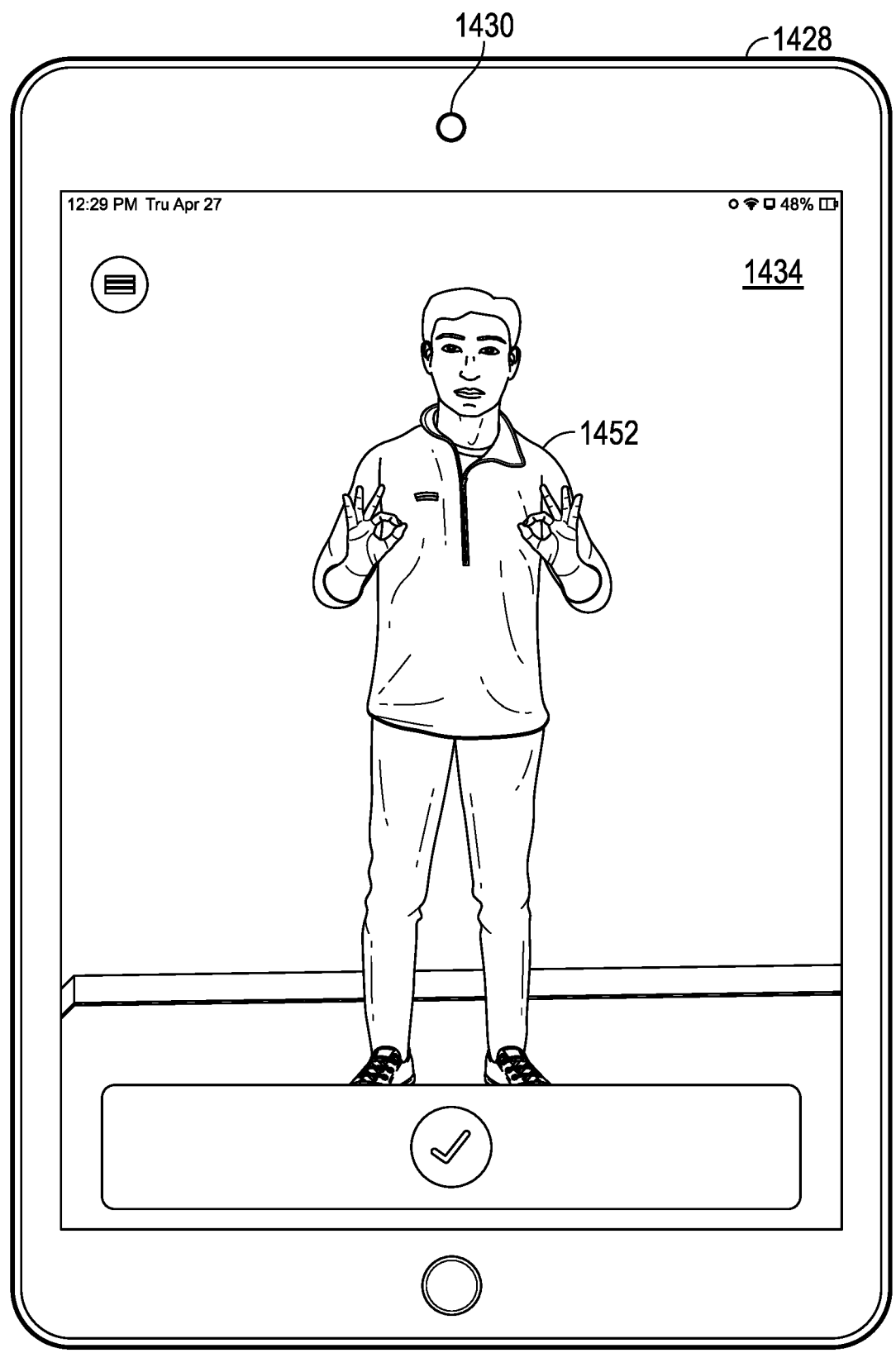
FIG. 21 depicts an example interface on a user computing device during an example exercise session.

Referring first to FIG. 19, at the initiation of an exercise session the user can receive instructions to properly position themselves within the field of view of the camera 1430. While FIG. 19 depicts the use of on-screen messaging, it is to be appreciated that instructions can be provided in any suitable format, such as auditory-based instructions. FIG. 20 depicts an example distance status bar that updates in real time as the user positions themselves further away from the camera 1430. Once it is determined that the user is at an appropriate distance from the camera 1430, an indication of successful positioning can be provided to the user, an example of which is presented in FIG. 21. Again, while FIG. 21 visually indicates successful positioning, other embodiments can additionally or alternatively use different types of indicators.

Figure 22:
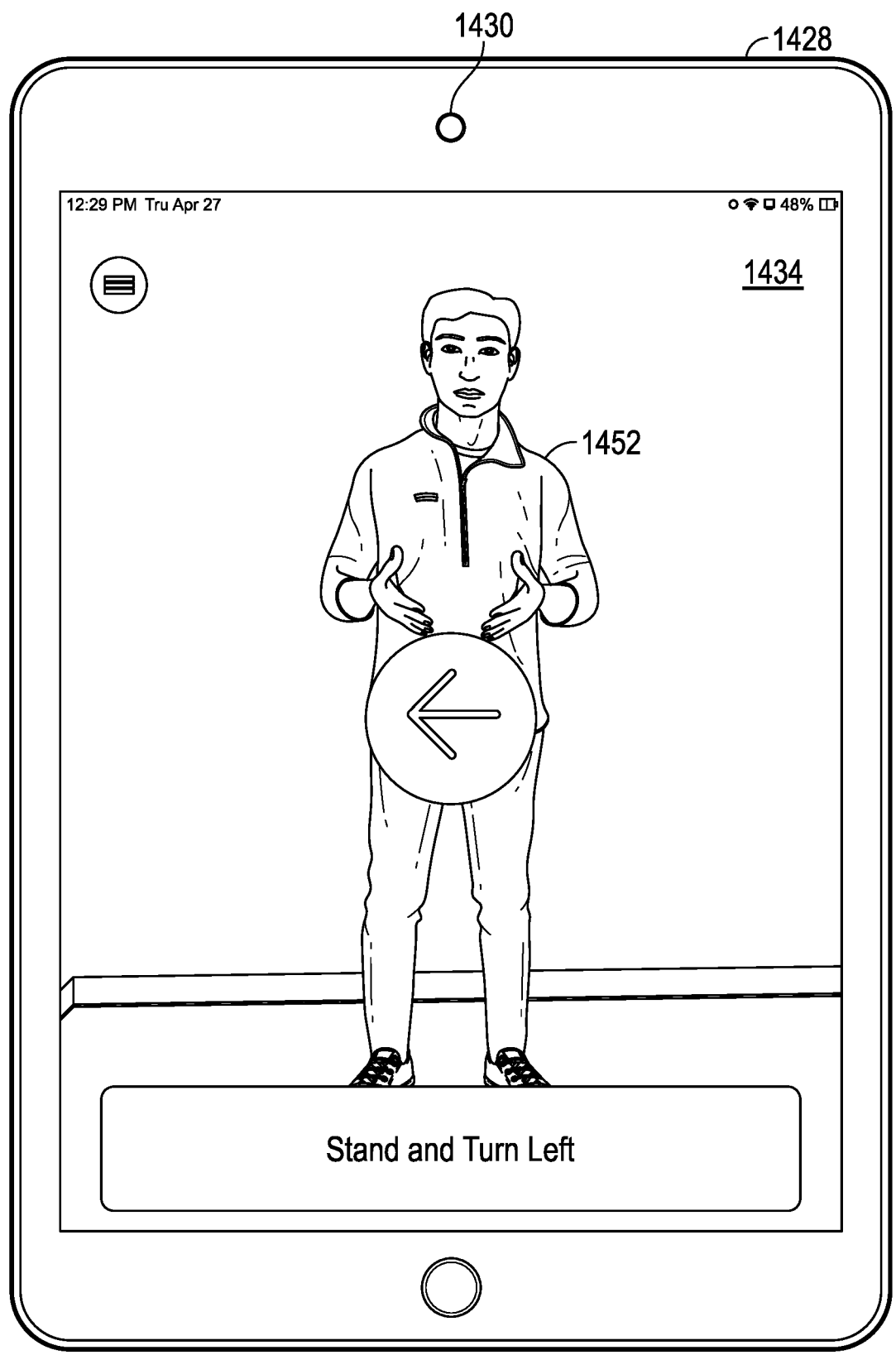
FIG. 22 depicts an example interface on a user computing device during an example exercise session.
Figure 23:
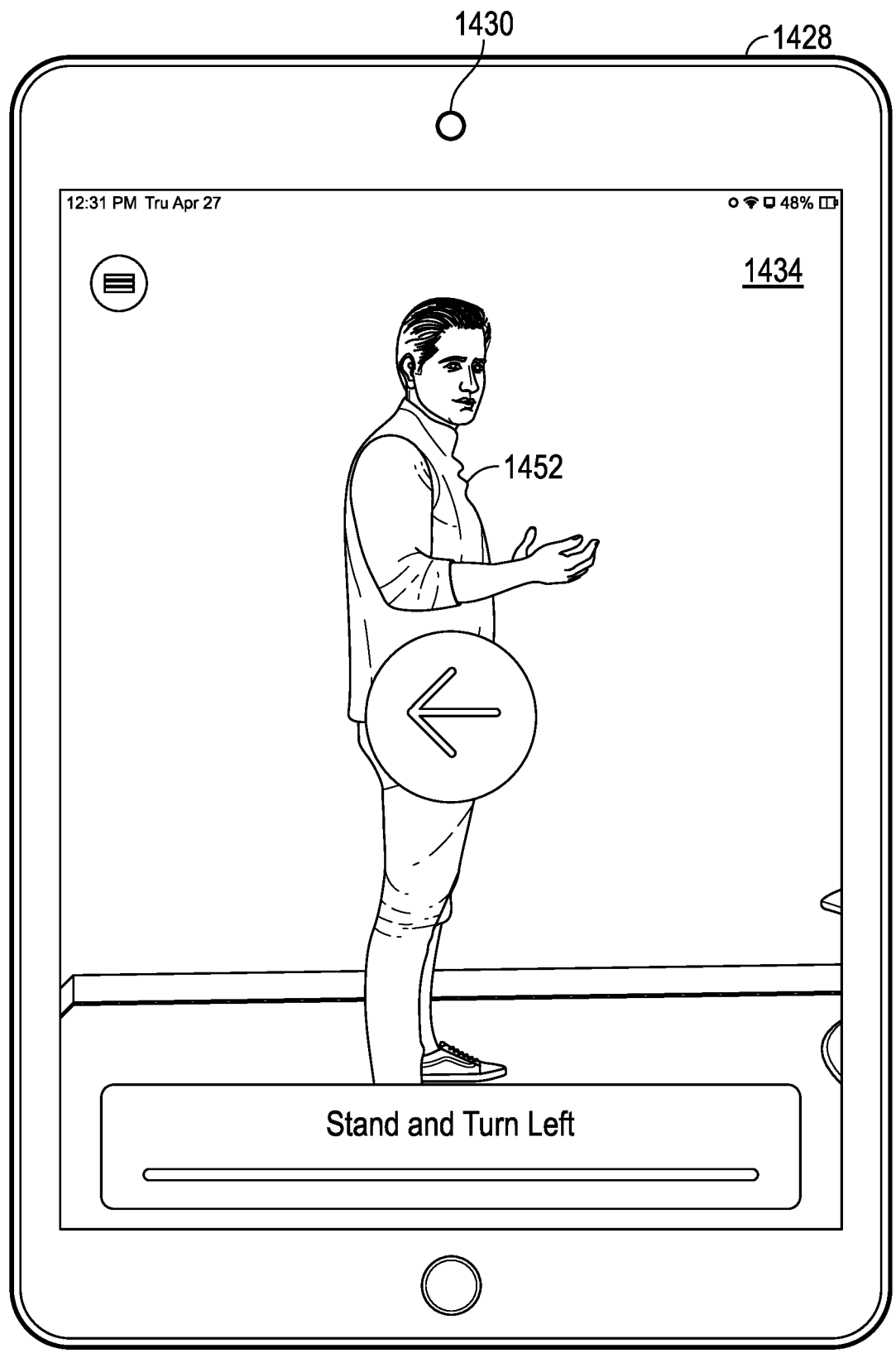
FIG. 23 depicts an example interface on a user computing device during an example exercise session.

Once the user is properly positioned, the user can be given instructions based on their personalized exercise protocol. For example, the user can be instructed to face a certain direction, sit down, lay down, use an accessory (such as a chair, a broomstick, or a wall, for example), and so forth. Referring to FIG. 22, based on the first exercise to be performed by the user in the illustrated example, the user is instructed to turn to their left. The user's movement can be tracked in real-time to measure compliance with the instruction. FIG. 23 illustrates that if the user turns the wrong direction, or otherwise does not comply with the instructions, the system will not progress to the next step.

Figure 24:
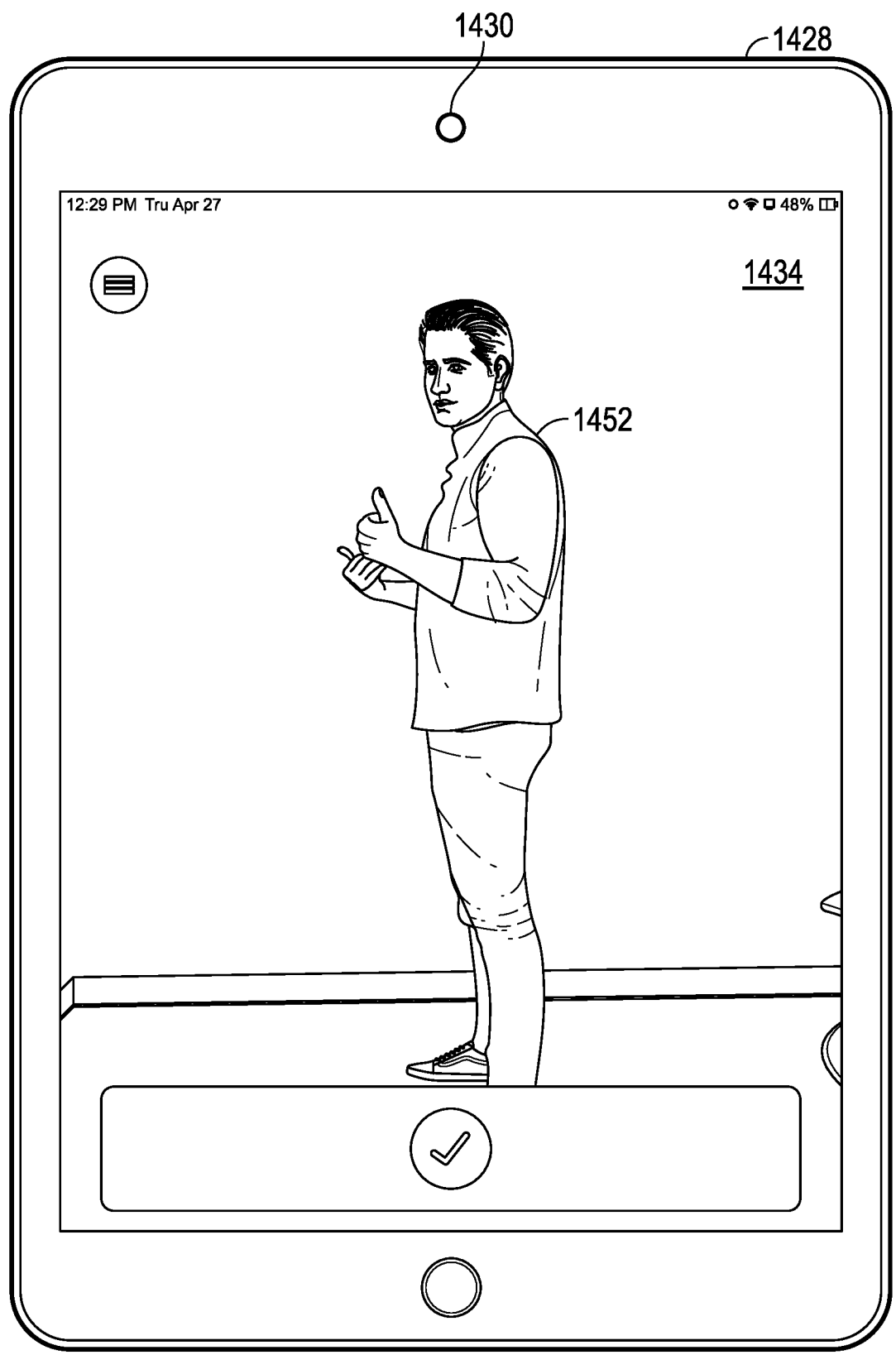
FIG. 24 depicts an example interface on a user computing device during an example exercise session.
Figure 25:
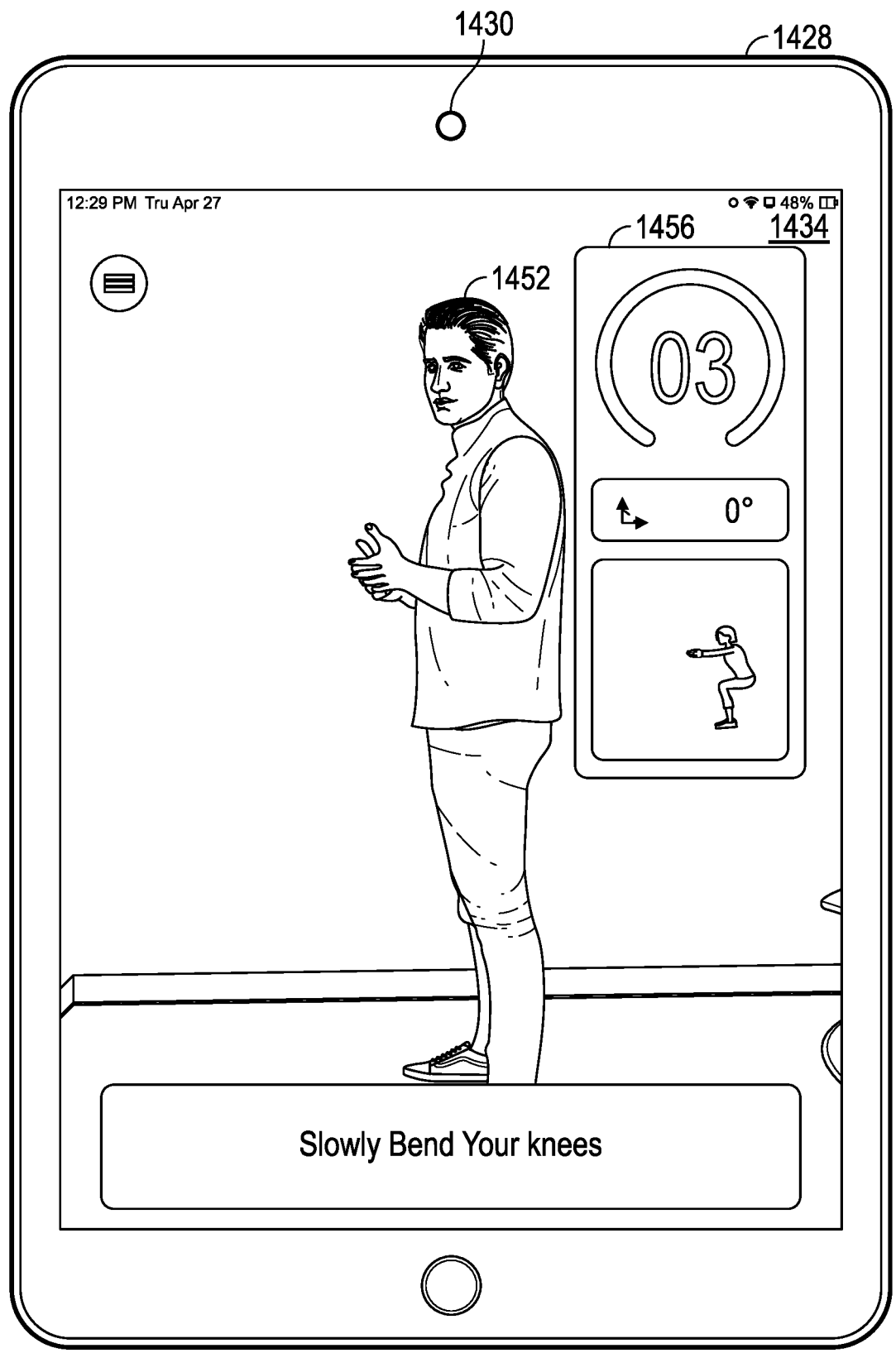
FIG. 25 depicts an example interface on a user computing device during an example exercise session.

FIG. 24 illustrates the interface when it has been detected that the user complied with the instructions. The user can then be prompted to perform a specific type of exercise (or movement) based on their exercise protocol. Referring to FIG. 25, an instruction panel 1456 is presented during the exercise. While a single instruction panel 1456 is shown in FIG. 25, it is to be appreciated that other embodiments can convey information to the user using different approaches, such as multiple panels, overlays (opaque or semi-transparent), scrolling tickers, and so forth. In the illustrated example, the instruction panel 1456 includes a range of motion graphic that updates in real-time, a repetition counter, additional real-time positional information (i.e. degree of range of motion), as well as an animation of the exercise to be performed.

Figure 26:
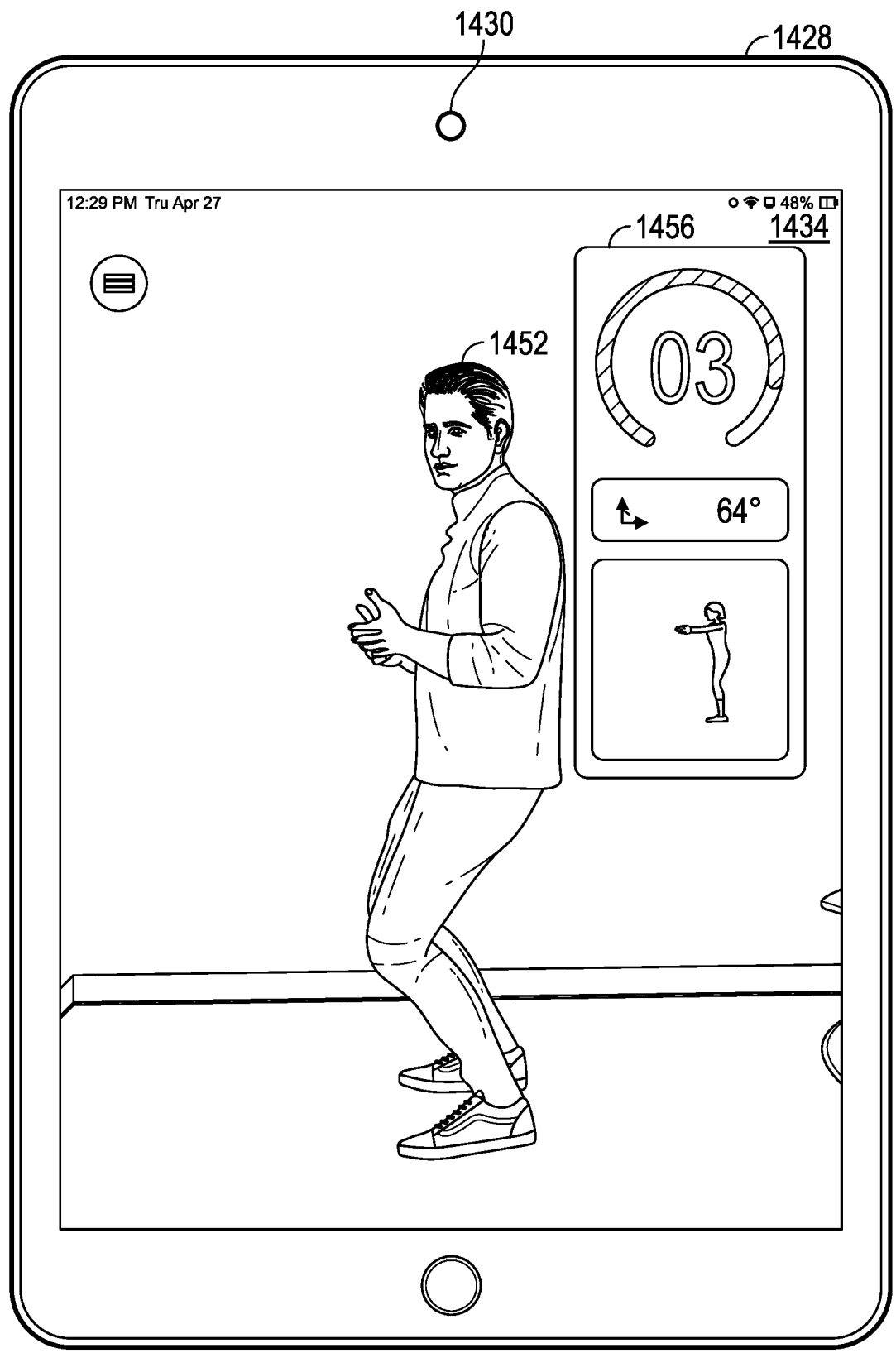
FIG. 26 depicts an example interface on a user computing device during an example exercise session.
Figure 27:
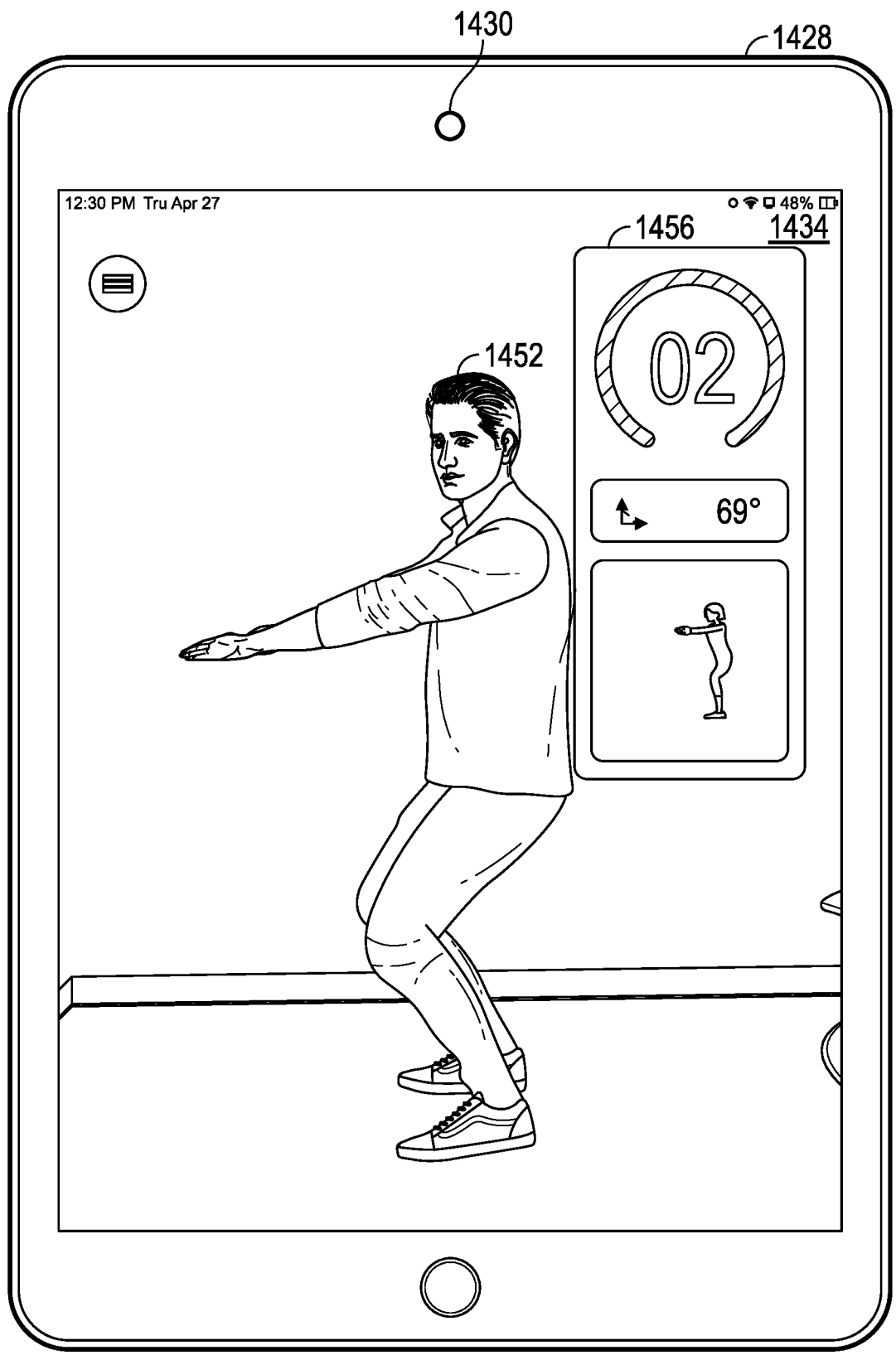
FIG. 27 depicts an example interface on a user computing device during an example exercise session.

FIG. 26 illustrates the interface 1434 mid-way through the exercise. As shown, the real-time range of motion graphic of FIG. 26, depicted as a horse shoe graphic, graphically conveys the user is completing a knee bend. The degree of range of motion percent indicates the user is at 64 degrees. In this embodiment, the degree of range of motion for this particular user for this particular exercise is set to 70 degrees. For a different user, the degree of range of motion can be set to a different value. In any event, upon successful completion of one repetition, the repetition can be counted, as shown in FIG. 27 where the repetition counter has decreased from "03" or "02". As is to be appreciated, while this use is instructed to complete 3 repetitions, other exercise protocols designed or otherwise provided to other user can instruct a different number of repetitions.

Figure 28:
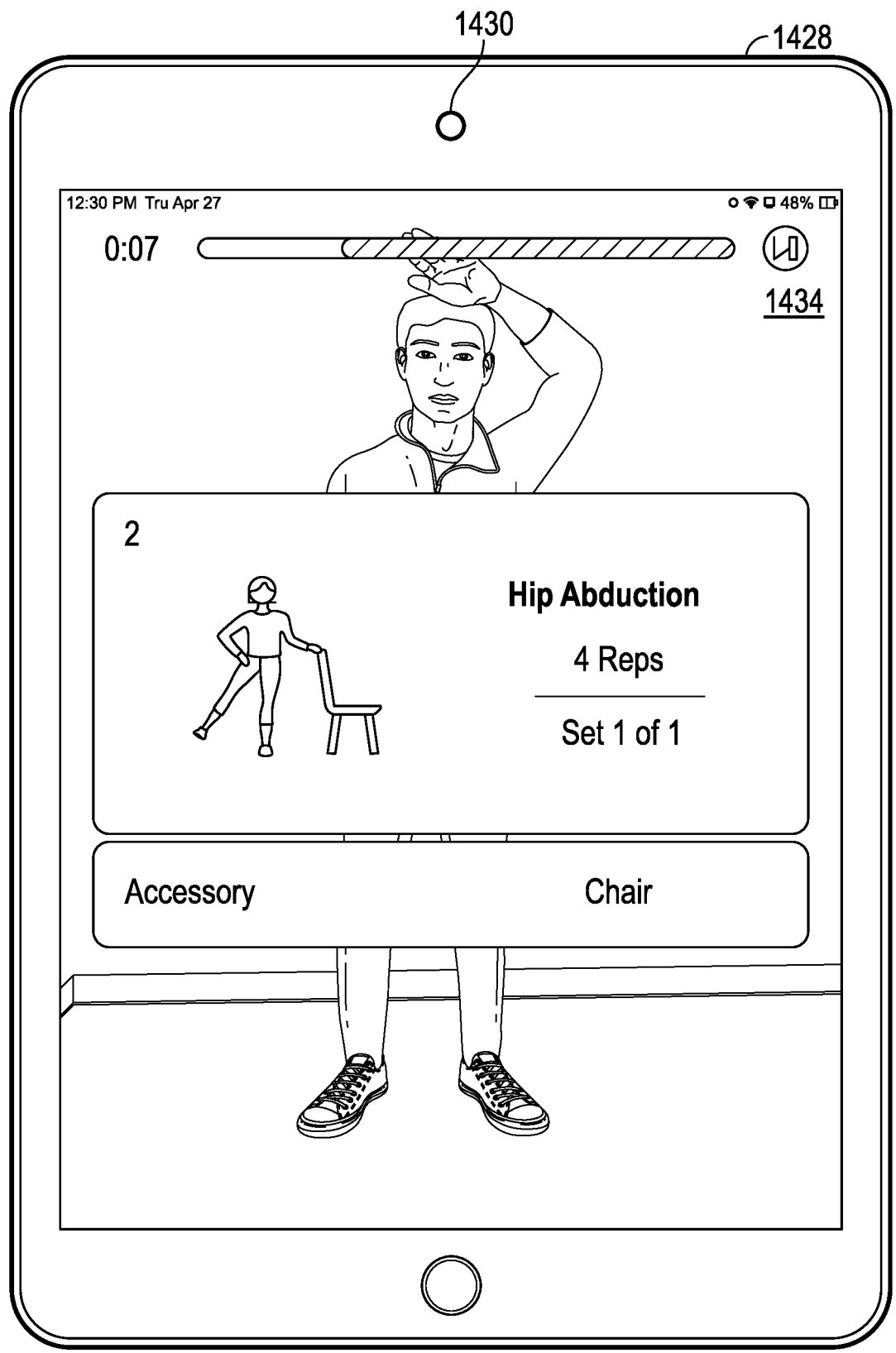
FIG. 28 depicts an example interface on a user computing device during an example exercise session.
Figure 29:
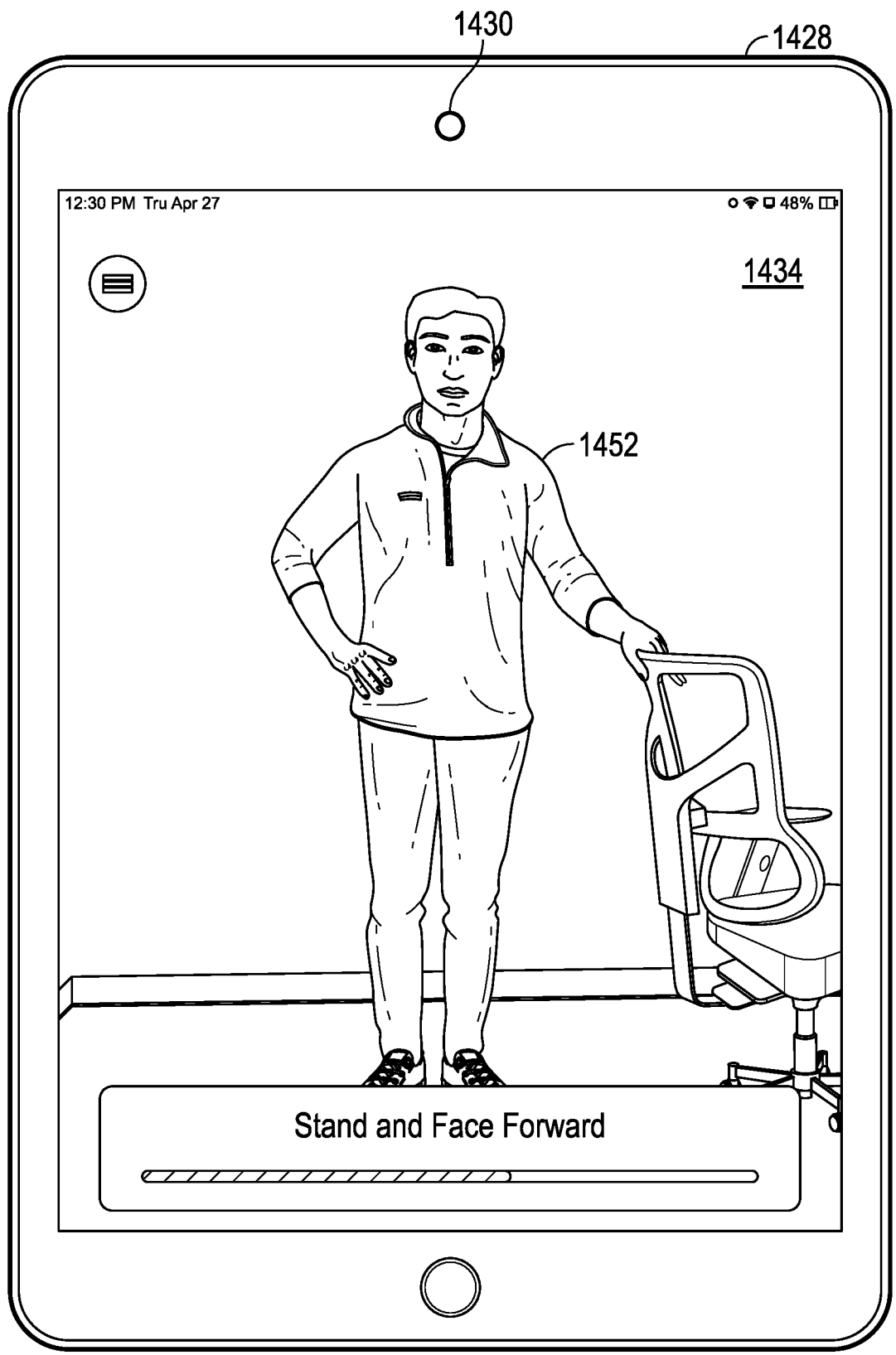
FIG. 29 depicts an example interface on a user computing device during an example exercise session.
Figure 30:
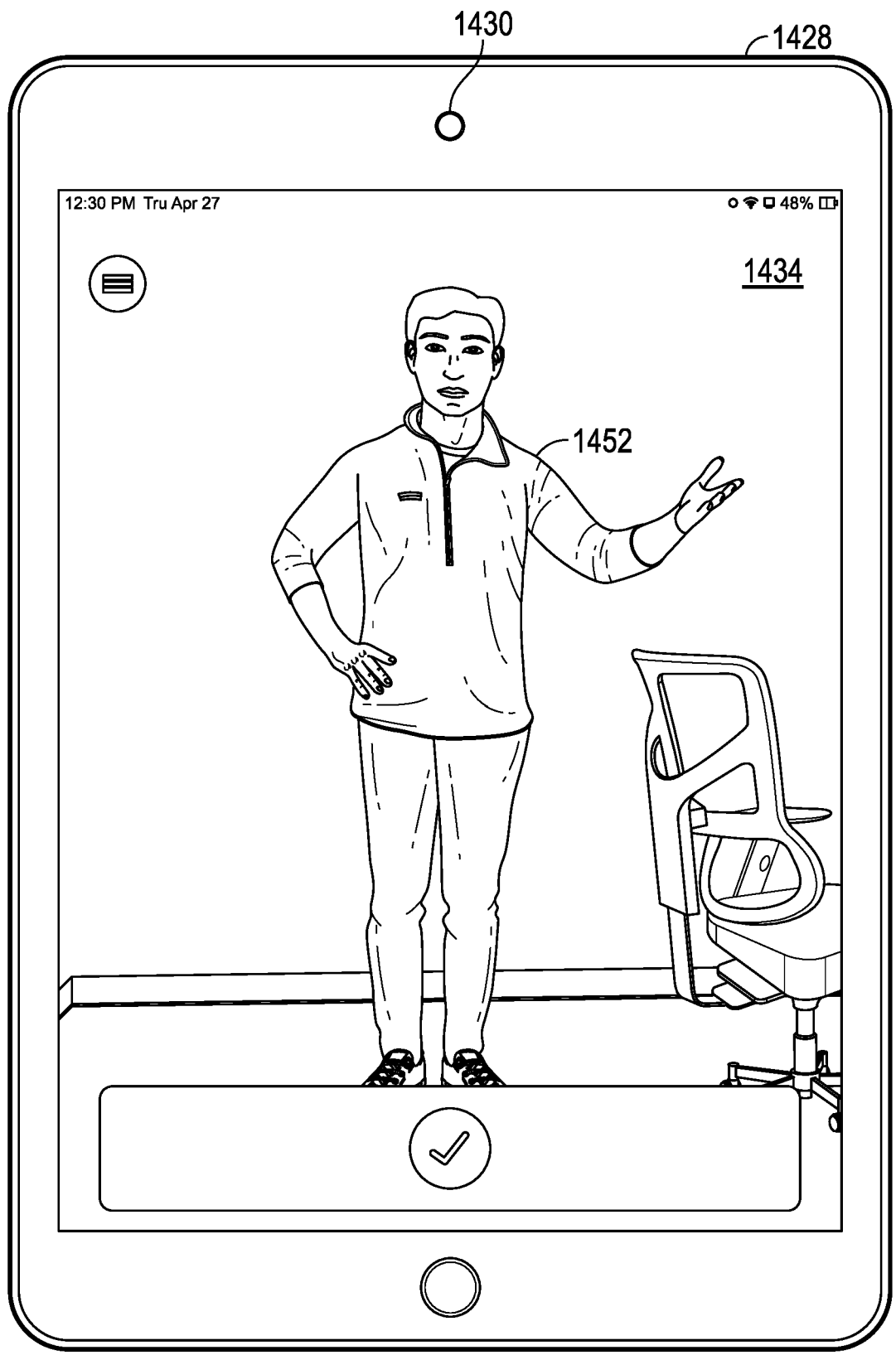
FIG. 30 depicts an example interface on a user computing device during an example exercise session.

Upon detecting that the user has completed the sufficient number of repetitions, the user can automatically be presented with the next exercise in their exercise protocol. FIG. 28 depicts an example exercise summary that can be provided to the user between exercises. As shown in FIG. 28, a graphic (or animation) of the exercise as well as additional information can be provided, such as the number of repetitions, the numbers of sets, any accessories that may be needed, and so forth. FIG. 29 shows another example instruction being provided to the user and the user's compliance with the instruction being measured, and an indication of successful compliance provided in FIG. 30.

Figure 31:
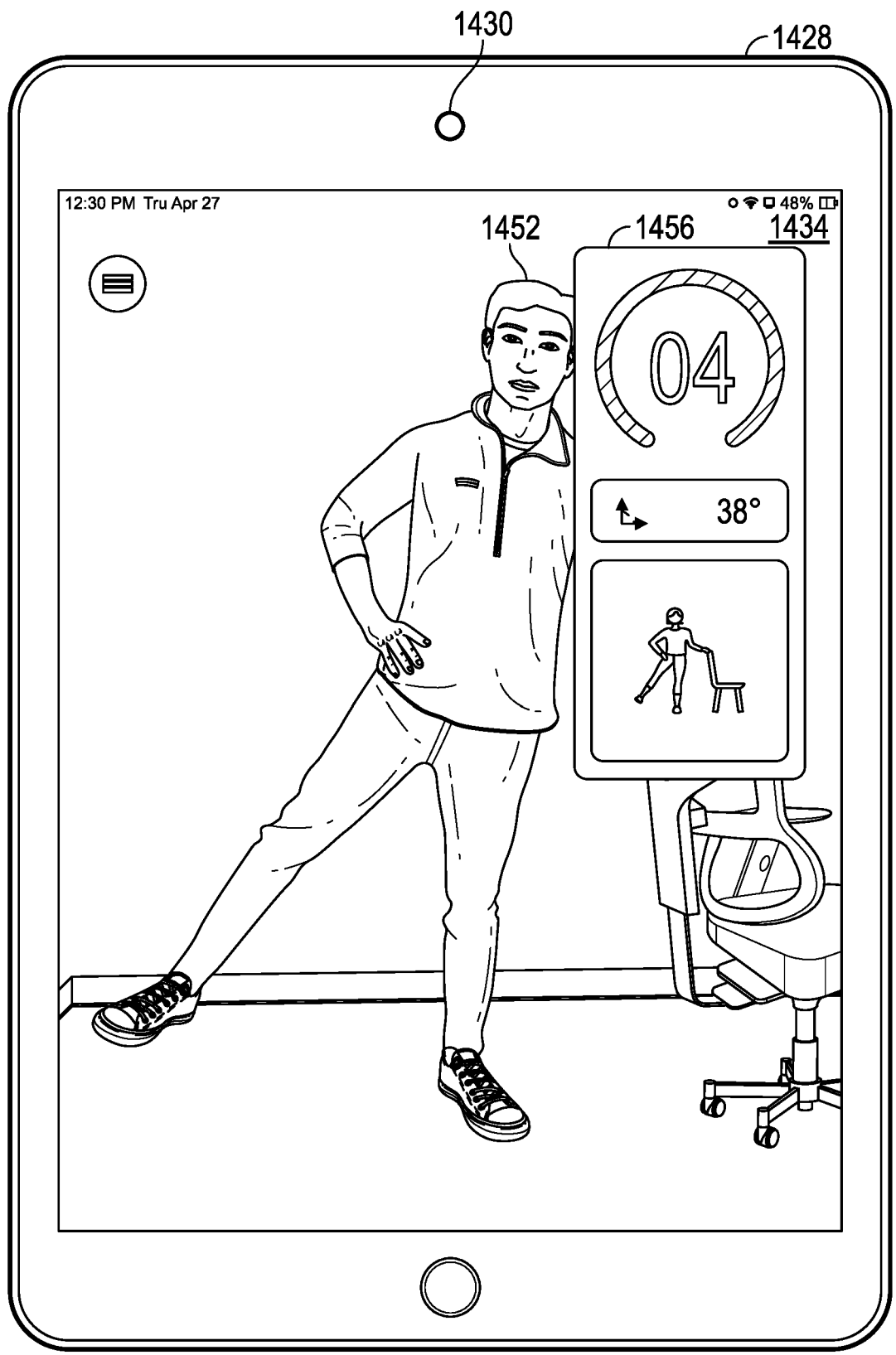
FIG. 31 depicts an example interface on a user computing device during an example exercise session.

FIG. 31 depicts another example use of the instruction panel 1456, which again includes a range of motion graphic that updates in real-time, a repetition counter, additional real-time positional information (i.e. degree of range of motion), as well as an animation of the exercise to be performed.

Figure 32:
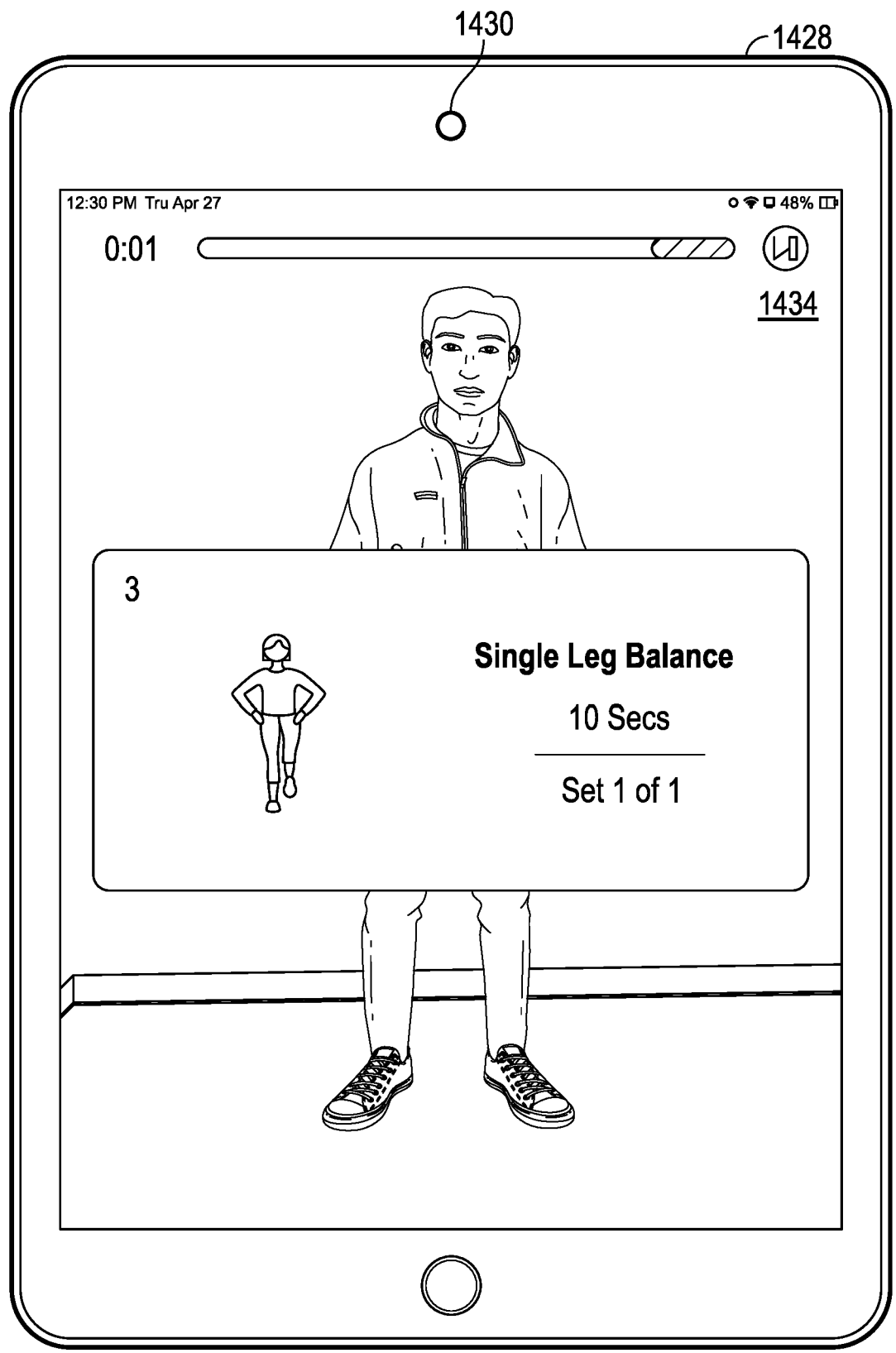
FIG. 32 depicts an example interface on a user computing device during an example exercise session.

Upon detecting that the user has completed the sufficient number of repetitions, the user can automatically be presented with the next exercise in their exercise protocol. FIG. 32 depicts an example exercise summary that can be provided to the user between exercises. As shown in FIG. 32, a graphic (or animation) of the exercise as well as additional information can be provided, such as the number of repetitions, the numbers of sets, and so forth.

Figure 33:
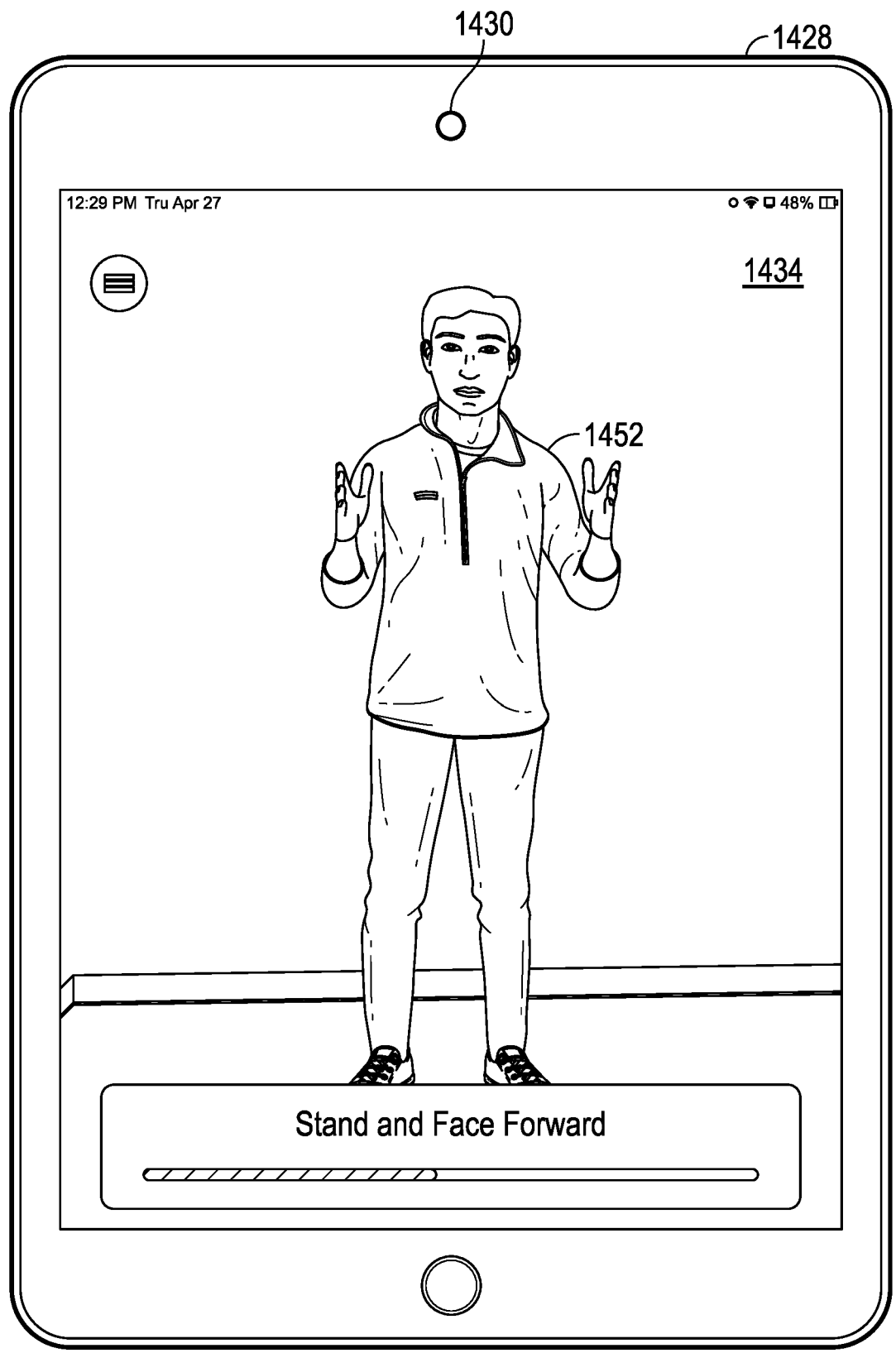
FIG. 33 depicts an example interface on a user computing device during an example exercise session.
Figure 34:
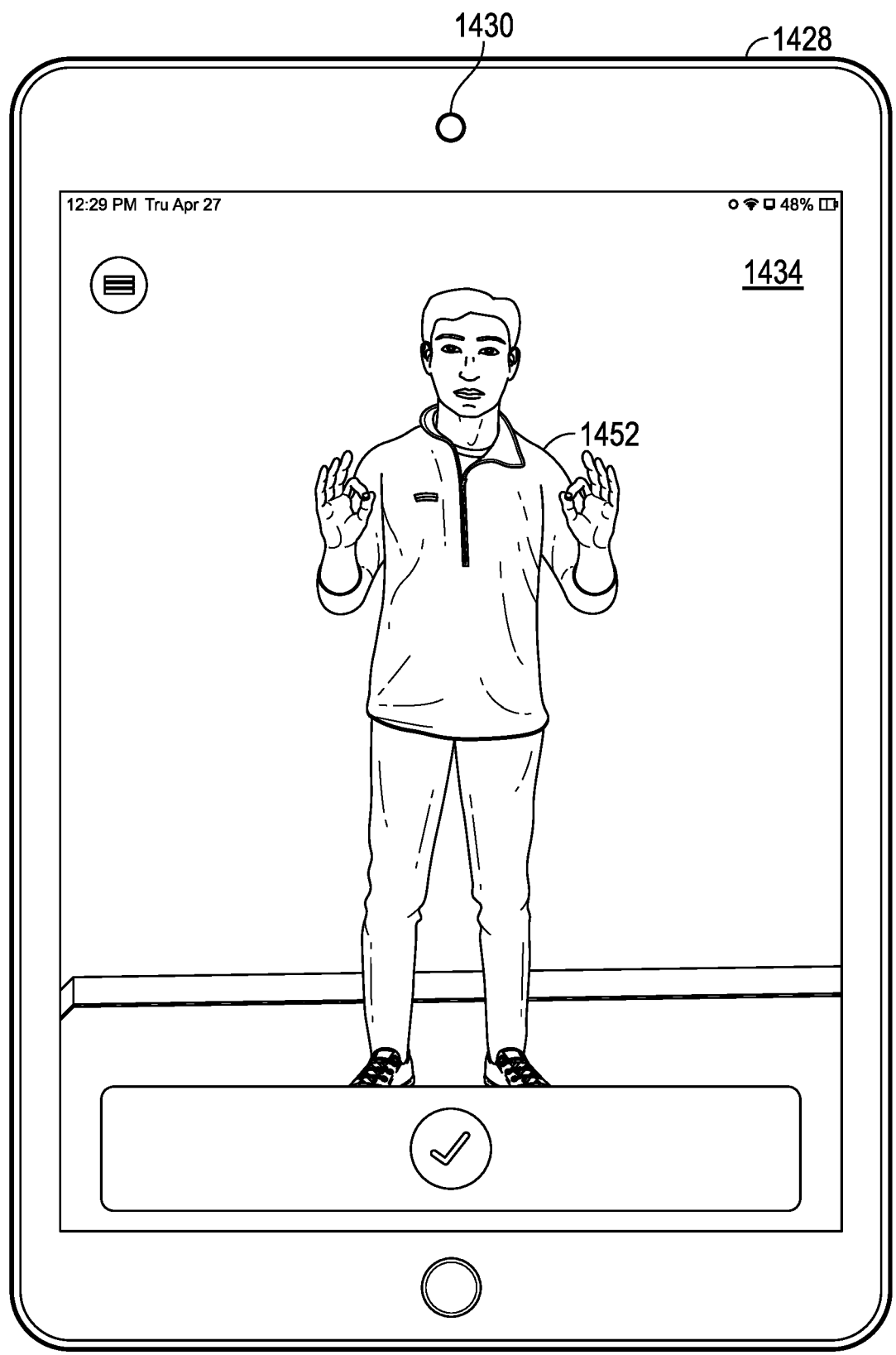
FIG. 34 depicts an example interface on a user computing device during an example exercise session.
Figure 35:
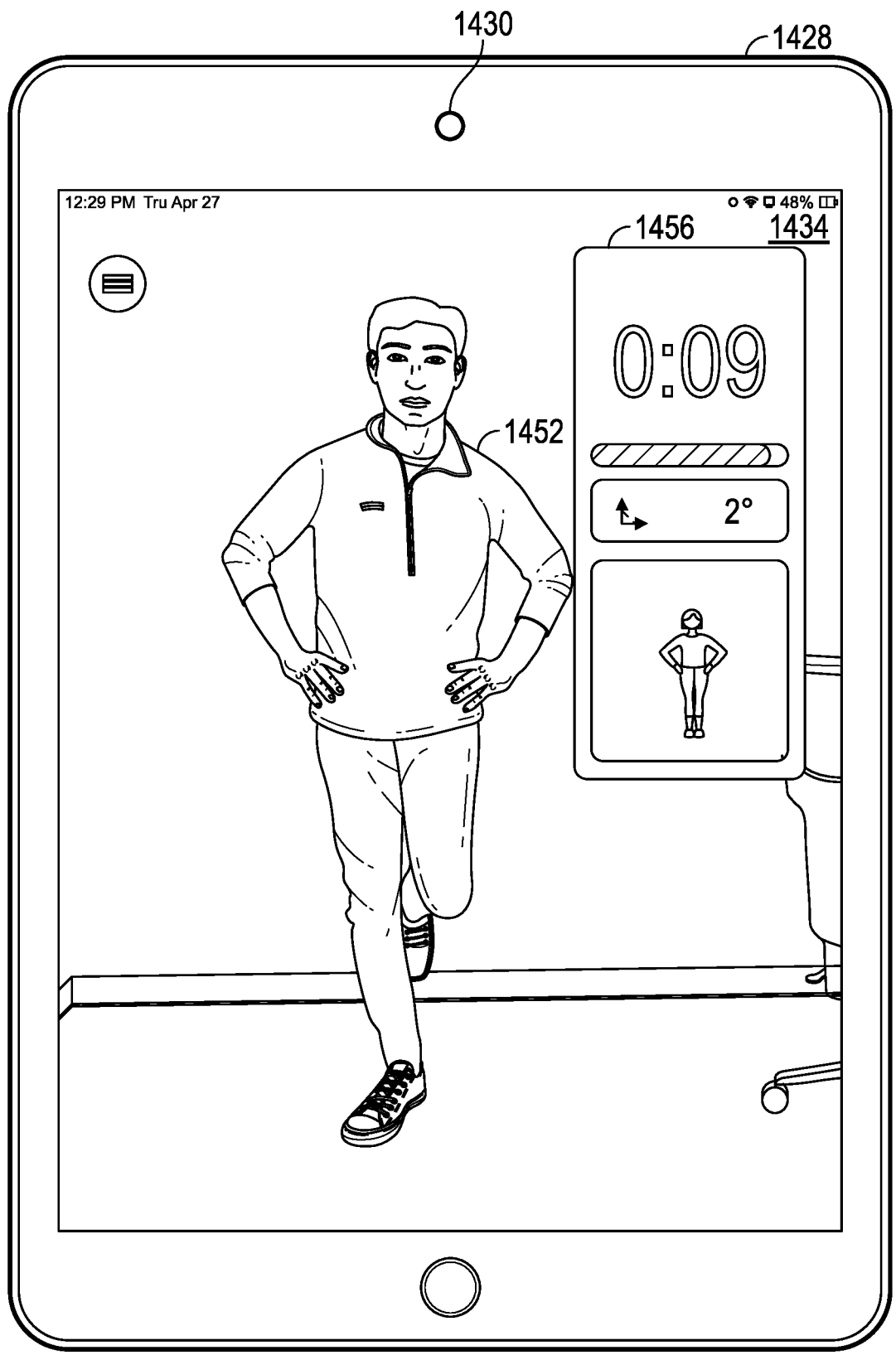
FIG. 35 depicts an example interface on a user computing device during an example exercise session.

FIG. 33 shows another example instruction being provided to the user and the user's compliance with the instruction being measured, and an indication of successful compliance provided in FIG. 34. FIG. 35 depicts another example use of the instruction panel 1456, which again includes a range of motion graphic that updates in real-time, a repetition counter, additional real-time positional information (i.e. degree of range of motion), as well as an animation of the exercise to be performed. As shown in FIG. 35, this particular exercise is time-based, so once it is detected the user has begun the exercise, the timer can automatically activate.

Figure 36:
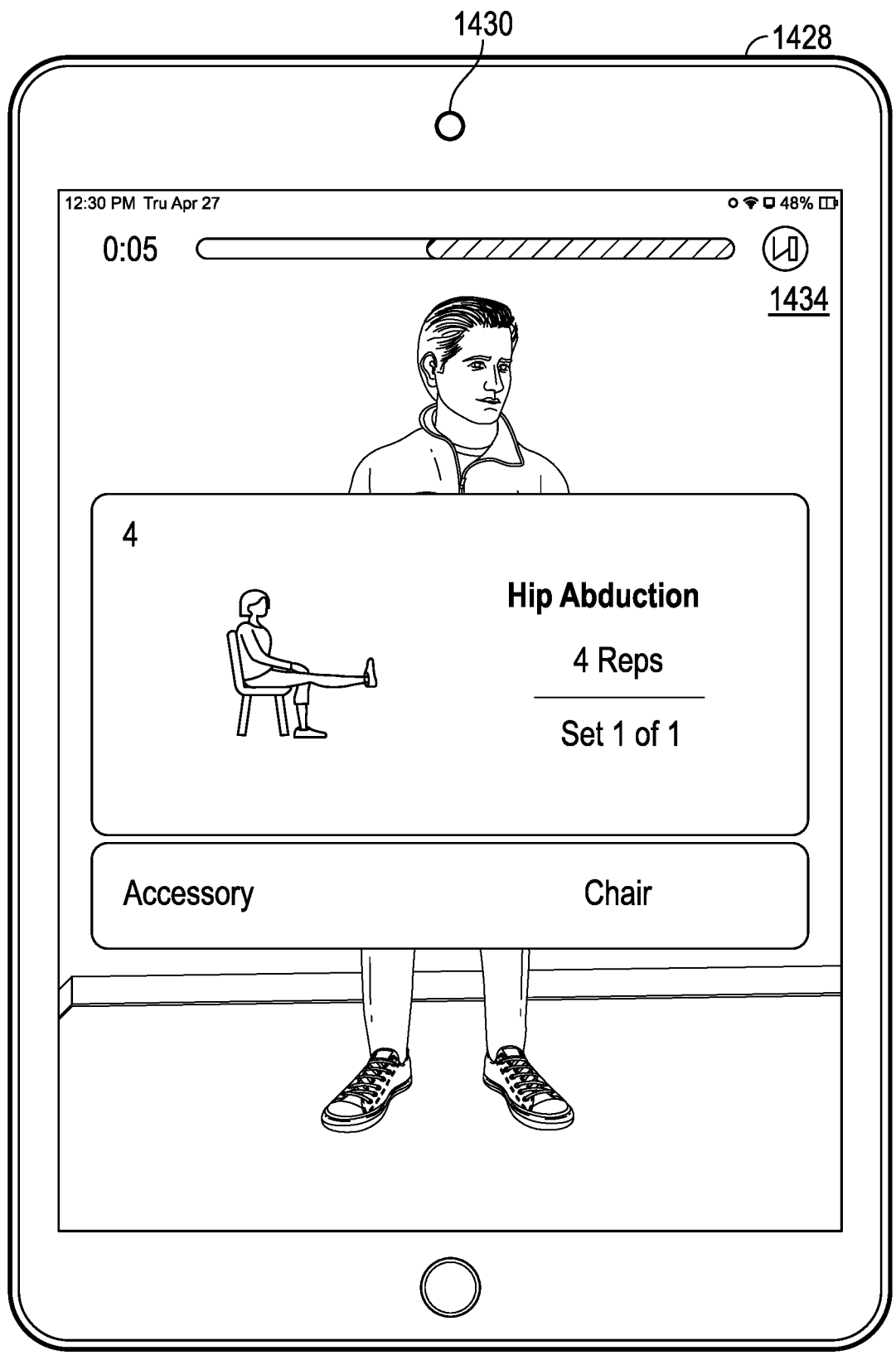
FIG. 36 depicts an example interface on a user computing device during an example exercise session.

Upon detecting that the user has completed the exercise, the user can automatically be presented with the next exercise in their exercise protocol. FIG. 36 depicts an example exercise summary that can be provided to the user between exercises. As shown in FIG. 36, a graphic (or animation) of the exercise as well as additional information can be provided, such as the number of repetitions, any needed accessories, the numbers of sets, and so forth.

Figure 37:
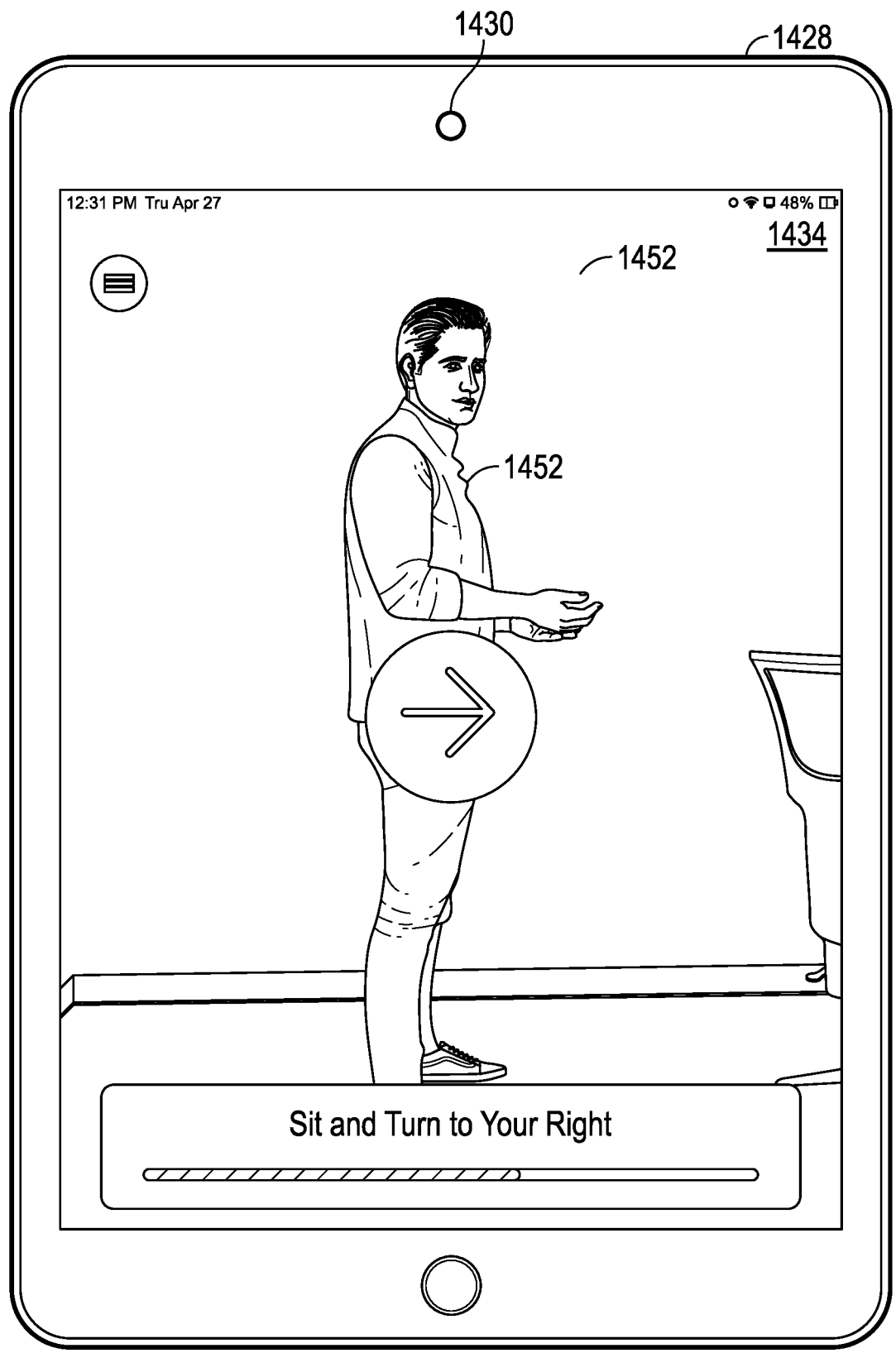
FIG. 37 depicts an example interface on a user computing device during an example exercise session.
Figure 38:
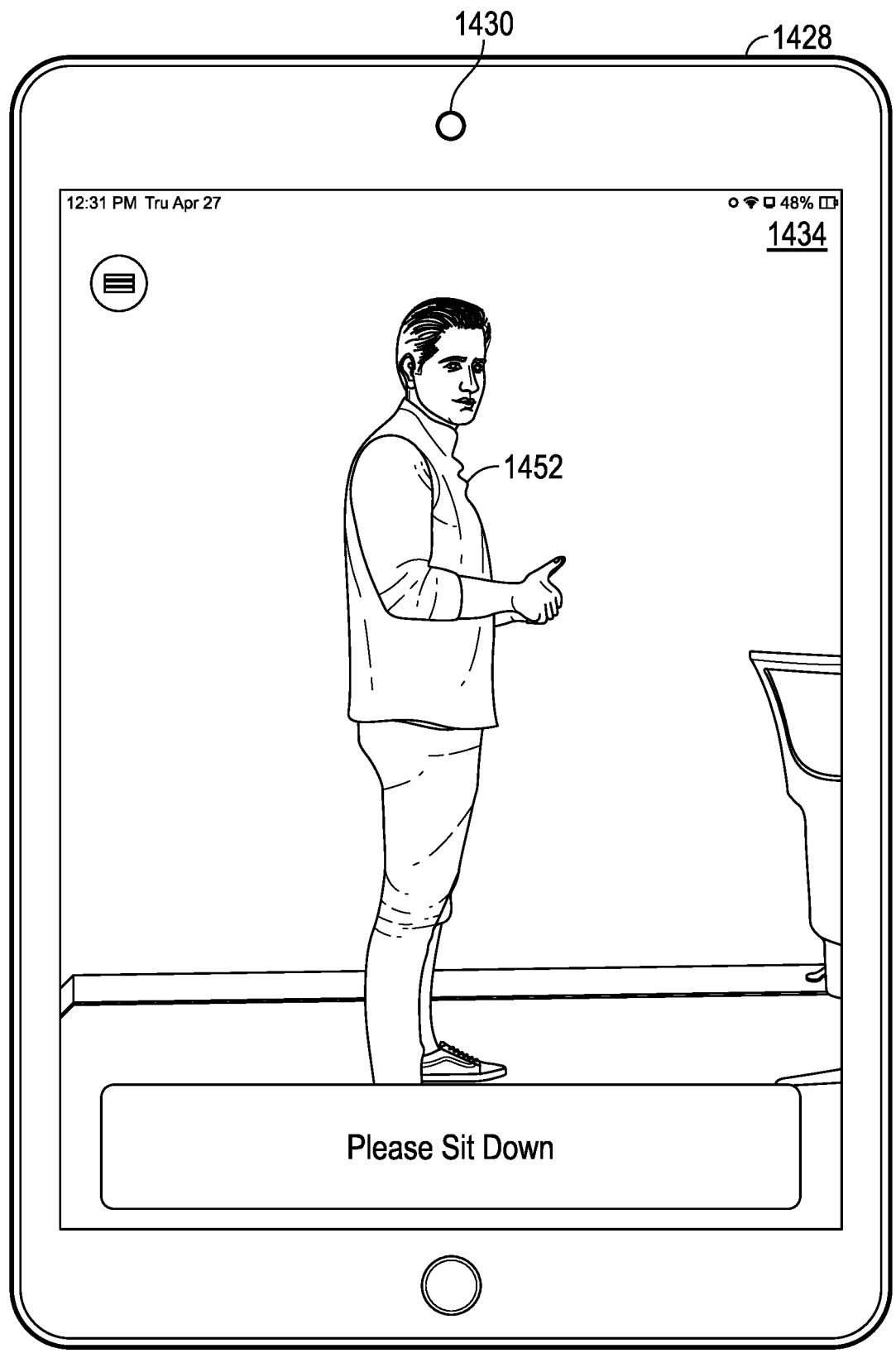
FIG. 38 depicts an example interface on a user computing device during an example exercise session.
Figure 39:
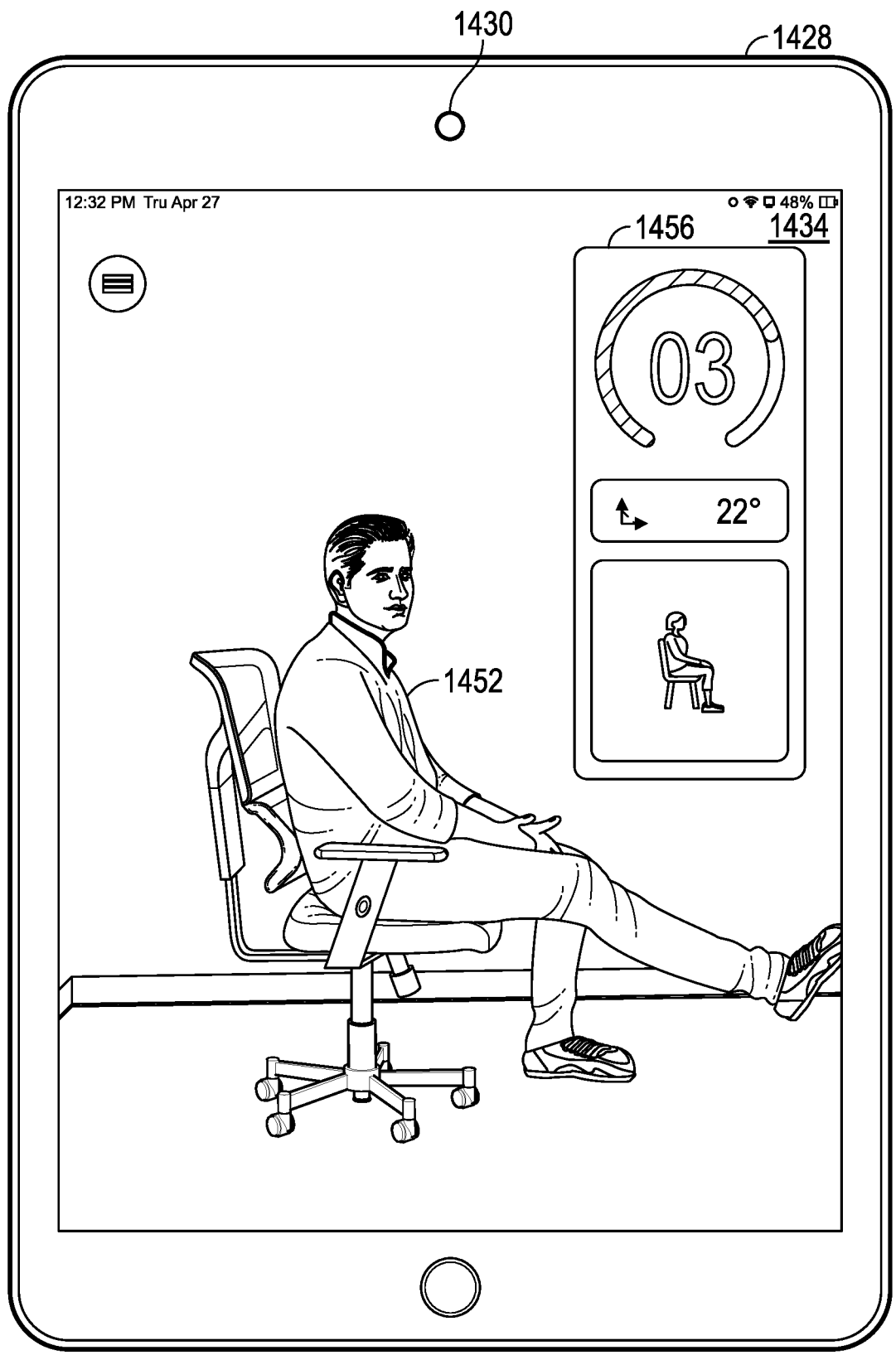
FIG. 39 depicts an example interface on a user computing device during an example exercise session.

FIG. 37 shows another example instruction being provided to the user and the user's compliance with the instruction being measured. This instruction is a two part instructions so compliance with both instructions can be measured. FIG. 38 depicts the user complying with the first instruction and then receiving an additional instruction, with compliance being required before advancement to the exercise. FIG. 39 depicts another example use of the instruction panel 1456, which again includes a range of motion graphic that updates in real-time, a repetition counter, additional real-time positional information (i.e. degree of range of motion), as well as an animation of the exercise to be performed.

Figure 40:
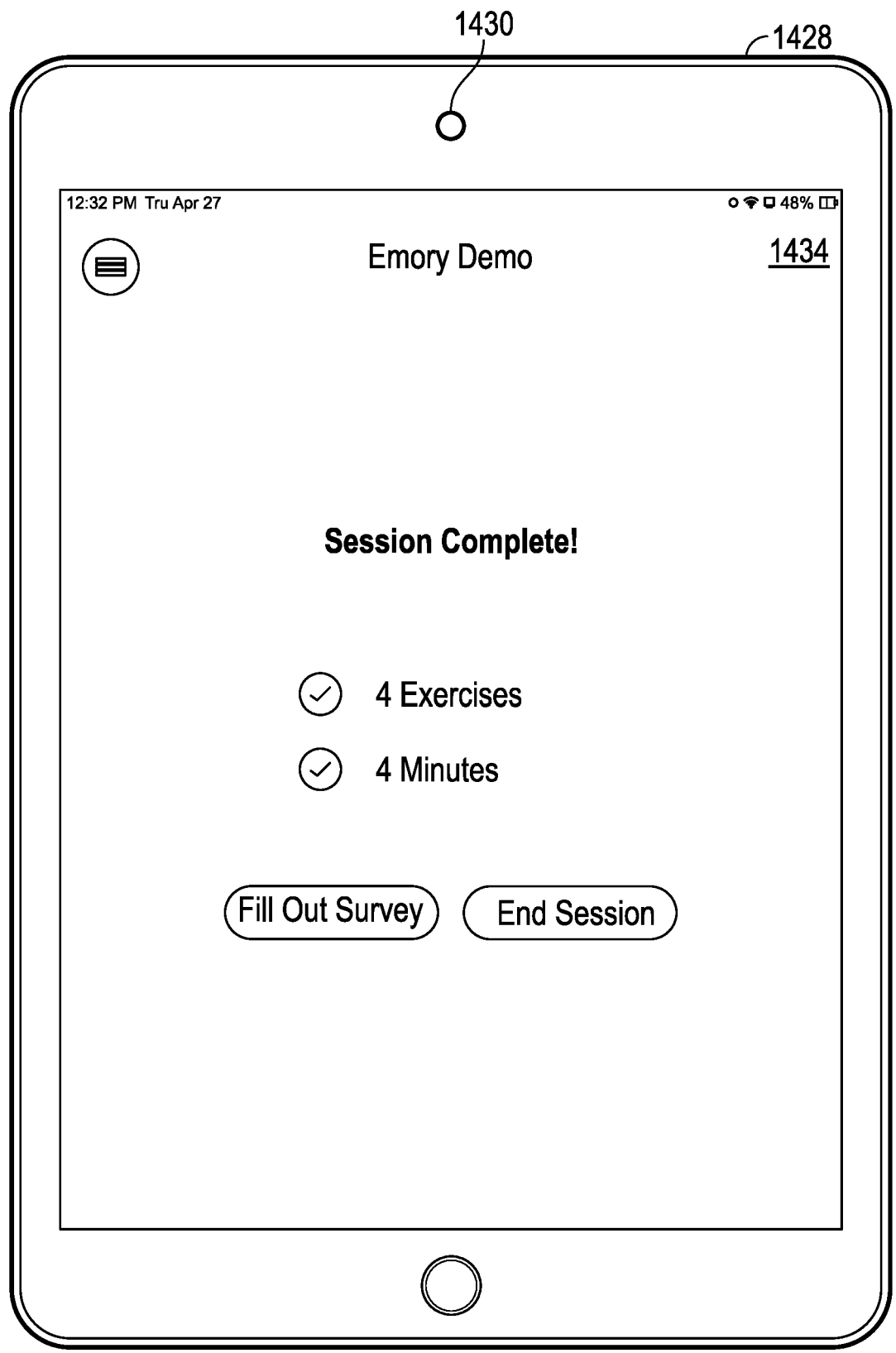
FIG. 40 depicts an example interface on a user computing device during an example exercise session.

Upon successful completion of the exercise protocol, a completed session summary can be provided to the user, as shown in FIG. 40. Notably, detailed information regarding the session can also be provided to the cloud-based fitness tracking computing system, such as range of motion information, duration information, as well as a wide variety of other information. Such information can be linked to the user's profile, as well used by the fitness tracking computing system for macro level data analysis and processing (i.e., based on the user's demographic, exercise protocol, and so forth).

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that these sorts of focused discussions would not facilitate a better understanding of the present invention, and therefore, a more detailed description of such elements is not provided herein.

Any element expressed herein as a means for performing a specified function is intended to encompass any way of performing that function including, for example, a combination of elements that performs that function. Furthermore the invention, as may be defined by such means-plus-function claims, resides in the fact that the functionalities provided by the various recited means are combined and brought together in a manner as defined by the appended claims. Therefore, any means that can provide such functionalities may be considered equivalents to the means shown herein. Moreover, the processes associated with the present embodiments may be executed by programmable equipment, such as computers. Software or other sets of instructions that may be employed to cause programmable equipment to execute the processes may be stored in any storage device, such as, for example, a computer system (non-volatile) memory, an optical disk, magnetic tape, or magnetic disk. Furthermore, some of the processes may be programmed when the computer system is manufactured or via a computer-readable memory medium.

It can also be appreciated that certain process aspects described herein may be performed using instructions stored on a computer-readable memory medium or media that direct a computer or computer system to perform process steps. A computer-readable medium may include, for example, memory devices such as diskettes, compact discs of both read-only and read/write varieties, optical disk drives, and hard disk drives. A non-transitory computer-readable medium may also include memory storage that may be physical, virtual, permanent, temporary, semi-permanent and/or semi-temporary.

These and other embodiments of the systems and methods can be used as would be recognized by those skilled in the art. The above descriptions of various systems and methods are intended to illustrate specific examples and describe certain ways of making and using the systems disclosed and described here. These descriptions are neither intended to be nor should be taken as an exhaustive list of the possible ways in which these systems can be made and used. A number of modifications, including substitutions of systems between or among examples and variations among combinations can be made. Those modifications and variations should be apparent to those of ordinary skill in this area after having read this disclosure.

What is claimed is:

1. A fitness tracking computing system comprising instructions stored in a memory, which when executed by one or more processors of the fitness tracking computing system, cause the fitness tracking computing system to:
   receive video data from a computing device via a communications network, wherein the computing device is operated by the user, wherein the computing device comprises a display and a camera, wherein the video data comprises metadata and images of the user collected the camera, and wherein the metadata comprises performance data of the camera and a screen resolution of the display;
   based on the metadata, adjust a setting of a body tracking model;
   cause a personalized movement instruction to be displayed on the display of the computing device;
   subsequent to adjusting the setting of the body tracking model, analyze the video data using the body tracking model to track real-time movements of the user to determine compliance with the personalized movement instruction; and
   cause visual feedback to be displayed on the display of the computing device.

2. The fitness tracking computing system of claim 1, wherein the instructions stored in a memory further cause the fitness tracking computing system to:
   receive a personalized exercise protocol associated with a user; and
   store the personalized exercise protocol in a data store.

3. The fitness tracking computing system of claim 1, wherein the personalized exercise protocol comprises an exercise protocol selected from a protocol library by a practitioner.

4. The fitness tracking computing system of claim 1, wherein the instructions stored in a memory further cause the fitness tracking computing system to:
generate reporting data for the user, wherein the reporting data comprises demographic data of the user and compliance data of the user.

5. The fitness tracking computing system of claim 1, wherein the camera is a built-in component of the computing device installed into the computing devices at time of manufacture.

6. The fitness tracking computing system of claim 1, wherein the visual feedback provides real-time range of motion feedback.

7. The fitness tracking computing system of claim 6, wherein the visual feedback provides a repetition counter.

8. The fitness tracking computing system of claim 7, wherein the instructions stored in a memory further cause the fitness tracking computing system to:
advance the repetition counter only when real-time movements of the user comply with the personalized movement instruction.

9. The fitness tracking computing system of claim 8, wherein determining compliance with the personalized movement instruction is based on a tolerance window.

10. The fitness tracking computing system of claim 1, wherein the visual feedback comprises a movement tolerance graphic correlated to the personalized exercise protocol, a movement reference indicator, and a real-time biometric marker graphical indicator.

11. The fitness tracking computing system of claim 10, wherein the instructions stored in a memory further cause the fitness tracking computing system to:
move the real-time biometric marker graphical indicator on the display relative to the movement tolerance graphic based on the real-time movements of the user.

12. The fitness tracking computing system of claim 11, wherein the instructions stored in a memory further cause the fitness tracking computing system to:
modify the visual appearance of the real-time biometric marker graphical indicator when the real-time biometric marker graphical indicator crosses the movement reference indicator.

13. The fitness tracking computing system of claim 1, wherein the setting is one or more of a video scale factor and a buffer length.

14. A fitness tracking computing system comprising instructions stored in a memory, which when executed by one or more processors of the fitness tracking computing system, cause the fitness tracking computing system to:
receive video data from a computing device via a web-based communications, wherein the computing device is executing a web browsing application, wherein the computing device comprises a display and a camera, and wherein the video data comprises metadata and images of a user of the computing device collected the camera;
based on the metadata, determine performance data of the camera and a screen resolution of the display;
based on at least one of the performance data of the camera and the screen resolution of the display, adjust a setting of a body tracking model;
cause a personalized movement instruction to be displayed on the display of the computing device;
subsequent to adjusting the setting of the body tracking model, analyze the video data using the body tracking model to track real-time movements of the user;
cause visual feedback to be displayed on the display of the computing device;
cause a repetition counter to be displayed on the display; and
advance the repetition counter only when real-time movements of the user are determined to comply with the personalized movement instruction.

15. The fitness tracking computing system of claim 14, wherein the camera is any of a built-in component of the computing device and a web camera connected to the computing device via a USB connection.

16. The fitness tracking computing system of claim 15, wherein the visual feedback provides real-time range of motion feedback.

17. The fitness tracking computing system of claim 16, wherein determining compliance with the personalized movement instruction is based on a tolerance window.

18. The fitness tracking computing system of claim 14, wherein the visual feedback comprises a movement tolerance graphic correlated to a movement reference indicator, and a real-time biometric marker graphical indicator.

19. A fitness tracking computing system comprising instructions stored in a memory, which when executed by one or more processors of the fitness tracking computing system, cause the fitness tracking computing system to:
receive video data from a computing device via a communications network, wherein the computing device is operated by the user, wherein the computing device comprises a display and a camera, and wherein the video data comprises images of the user collected the camera;
determine an operational parameter of the computing device;
based on the operational parameter of the computing device, adjust a setting of a body tracking model;
cause a personalized movement instruction to be displayed on the display of the computing device;
subsequent to adjusting the setting of the body tracking model, analyze the video data using the body tracking model to track real-time movements of the user to determine compliance with the personalized movement instruction; and
cause visual feedback to be displayed on the display of the computing device, wherein the visual feedback provides real-time range of motion feedback.

20. The fitness tracking computing system of claim 19, wherein the visual feedback provides a repetition counter, and wherein the instructions stored in a memory further cause the fitness tracking computing system to:
advance the repetition counter only when real-time movements of the user comply with the personalized movement instruction.

* * * * *

UNITED STATES PATENT AND TRADEMARK OFFICE
CERTIFICATE OF CORRECTION

PATENT NO. : 12,172,052 B2
APPLICATION NO. : 18/134281
DATED : December 24, 2024
INVENTOR(S) : James Ryan Eder Page 1 of 1

It is certified that error appears in the above-identified patent and that said Letters Patent is hereby corrected as shown below:

In the Claims

Column 20, Claim 1, Lines 43-44, change "collected the camera" to --collected by the camera--;
Column 21, Claim 14, Lines 55-56, change "collected the camera" to --collected by the camera--; and
Column 22, Claim 19, Lines 35-36, change "collected the camera" to --collected by the camera--.

Signed and Sealed this
Fifteenth Day of July, 2025

Coke Morgan Stewart
*Acting Director of the United States Patent and Trademark Office*